(12) United States Patent
Gomi et al.

(10) Patent No.: US 9,561,049 B2
(45) Date of Patent: Feb. 7, 2017

(54) FLUID EJECTION DEVICE

(71) Applicant: SEIKO EPSON CORPORATION, Tokyo (JP)

(72) Inventors: Masaki Gomi, Hino (JP); Hiroyuki Yoshino, Suwa (JP)

(73) Assignee: SEIKO EPSON CORPORATION, Tokyo (JP)

( * ) Notice: Subject to any disclaimer, the term of this patent is extended or adjusted under 35 U.S.C. 154(b) by 109 days.

(21) Appl. No.: 14/682,983

(22) Filed: Apr. 9, 2015

(65) Prior Publication Data

US 2015/0289898 A1 Oct. 15, 2015

(30) Foreign Application Priority Data

Apr. 10, 2014 (JP) .................................. 2014-080828

(51) Int. Cl.
*A61B 17/3203* (2006.01)

(52) U.S. Cl.
CPC ................................ *A61B 17/3203* (2013.01)

(58) Field of Classification Search
CPC ..................... A61B 17/3203; A61B 17/32037; A61B 2017/32032; A61B 2017/32035; A61M 2205/3334; A61M 2205/3389; A61M 3/0233; A61M 3/0237; A61M 3/025; A61M 3/0254; A61M 3/0258; A61M 3/0262
See application file for complete search history.

(56) References Cited

U.S. PATENT DOCUMENTS

| | | | | | |
|---|---|---|---|---|---|
| 5,259,842 | A | * | 11/1993 | Plechinger | A61B 17/3203 222/334 |
| 5,505,729 | A | * | 4/1996 | Rau | A61B 17/3203 604/22 |
| 5,871,462 | A | * | 2/1999 | Yoder | A61B 17/1644 604/22 |
| 7,278,721 | B2 | * | 10/2007 | Shimizu | B41J 2/17546 347/49 |
| 7,942,489 | B2 | * | 5/2011 | Ushinohama | B41J 2/04505 347/10 |
| 8,382,702 | B2 | * | 2/2013 | Uchida | A61B 17/3203 604/118 |
| 8,919,664 | B2 | * | 12/2014 | Seto | A61B 17/3203 239/101 |

(Continued)

FOREIGN PATENT DOCUMENTS

JP 2013-213422 A 10/2013

*Primary Examiner* — Ryan J Severson
(74) *Attorney, Agent, or Firm* — Maschoff Brennan

(57) ABSTRACT

A fluid ejection device includes a fluid accommodation portion having an outlet and a fluid pressing unit that causes the fluid to flow out of the fluid outlet through a channel. A fluid ejection unit ejects in a pulsed manner the fluid received from a fluid intake port connected to the channel. A pressure detection unit detects an inner pressure of the fluid accommodation portion. A press control unit controls the inner pressure of the fluid accommodation portion to approach a target pressure value when the channel is closed. A channel determination unit determines that the channel is not closed if a detected movement speed of the fluid pressing unit is a predetermined speed or greater when a predetermined amount of time has elapsed after a difference between the inner pressure of the fluid accommodation portion and the target pressure value becomes less than a predetermined value.

4 Claims, 8 Drawing Sheets

(56) References Cited

U.S. PATENT DOCUMENTS

| | | | |
|---|---|---|---|
| 9,005,227 B2* | 4/2015 | Kojima | A61B 17/3203 606/167 |
| 9,168,056 B2* | 10/2015 | Uchida | A61B 17/3203 |
| 9,174,435 B2* | 11/2015 | Yoshino | B41J 2/04541 |
| 9,204,890 B2* | 12/2015 | Asahi | A61B 17/3203 |
| 9,237,901 B2* | 1/2016 | Asahi | A61B 17/3203 |
| 9,238,373 B2* | 1/2016 | Gomi | B41J 2/17596 |
| 9,248,654 B2* | 2/2016 | Gomi | B41J 2/175 |
| 9,296,213 B2* | 3/2016 | Gomi | A61B 17/3203 |
| 9,352,082 B2* | 5/2016 | Uchida | A61M 5/1422 |
| 9,352,574 B2* | 5/2016 | Gomi | B41J 2/175 |
| 9,402,946 B2* | 8/2016 | Seto | A61B 17/3203 |
| 2002/0045911 A1* | 4/2002 | Fletcher | A61B 17/3203 606/167 |
| 2005/0244301 A1* | 11/2005 | Fletcher | A61B 17/3203 422/400 |
| 2009/0043480 A1* | 2/2009 | Seto | A61B 17/3203 701/103 |
| 2010/0078495 A1* | 4/2010 | Seto | A61B 17/3203 239/1 |
| 2010/0245495 A1* | 9/2010 | Katada | B41J 2/515 347/85 |
| 2011/0006127 A1* | 1/2011 | Ono | A61B 17/3203 239/1 |
| 2011/0036859 A1* | 2/2011 | Matsuzaki | A61B 17/3203 604/131 |
| 2011/0054505 A1* | 3/2011 | Kojima | A61B 17/3203 606/167 |
| 2011/0194945 A1* | 8/2011 | Kensy | A61B 17/3203 417/26 |
| 2011/0208224 A1* | 8/2011 | Kojima | F04B 43/04 606/167 |
| 2012/0046605 A1* | 2/2012 | Uchida | A61B 17/3203 604/65 |
| 2012/0095401 A1* | 4/2012 | Uchida | A61B 17/3203 604/151 |
| 2012/0176431 A1* | 7/2012 | Kojima | A61B 17/3203 347/14 |
| 2012/0181352 A1* | 7/2012 | Seto | A61B 17/3203 239/101 |
| 2013/0038654 A1* | 2/2013 | Yoshino | B41J 2/04541 347/10 |
| 2013/0064698 A1* | 3/2013 | Oshima | F04B 43/046 417/410.1 |
| 2013/0096601 A1* | 4/2013 | Asahi | A61B 17/3203 606/190 |
| 2013/0144321 A1* | 6/2013 | Uchida | A61B 17/3203 606/190 |
| 2013/0158544 A1* | 6/2013 | Kuhner | A61B 17/3203 606/39 |
| 2013/0243616 A1* | 9/2013 | Seto | F04B 43/095 417/212 |
| 2014/0127037 A1* | 5/2014 | Uchida | F04B 11/005 417/53 |
| 2014/0134001 A1* | 5/2014 | Uchida | A61M 5/1422 417/53 |
| 2014/0296892 A1* | 10/2014 | Uchida | B05B 5/16 606/167 |
| 2014/0296896 A1* | 10/2014 | Kojima | A61B 17/3203 606/167 |
| 2015/0073453 A1* | 3/2015 | Kojima | A61B 17/3203 606/167 |
| 2015/0075367 A1* | 3/2015 | Seto | A61B 17/3203 92/96 |
| 2015/0238216 A1* | 8/2015 | Uchida | A61B 17/3203 606/167 |
| 2015/0282830 A1* | 10/2015 | Miyazaki | A61B 17/3203 606/167 |
| 2015/0283809 A1* | 10/2015 | Miyazaki | B41J 2/04551 347/47 |
| 2015/0289894 A1* | 10/2015 | Miyazaki | A61B 17/3203 606/170 |
| 2015/0289895 A1* | 10/2015 | Gomi | A61B 17/3203 606/167 |
| 2015/0289896 A1* | 10/2015 | Gomi | A61B 17/3203 606/167 |
| 2015/0289897 A1* | 10/2015 | Gomi | A61B 17/3203 606/167 |
| 2015/0289898 A1* | 10/2015 | Gomi | A61B 17/3203 606/170 |
| 2015/0289899 A1* | 10/2015 | Asahi | A61B 17/3203 606/167 |
| 2015/0289900 A1* | 10/2015 | Asahi | A61B 17/3203 606/167 |
| 2015/0290933 A1* | 10/2015 | Asahi | A61B 17/3203 347/9 |
| 2015/0290942 A1* | 10/2015 | Gomi | A61B 17/3203 347/85 |
| 2015/0290943 A1* | 10/2015 | Gomi | B41J 2/175 347/85 |
| 2015/0290944 A1* | 10/2015 | Gomi | B41J 2/175 347/7 |
| 2015/0290949 A1* | 10/2015 | Gomi | B41J 2/17596 347/85 |
| 2015/0293538 A1* | 10/2015 | Asahi | A61B 17/3203 700/283 |
| 2016/0008021 A1* | 1/2016 | Yoshino | B41J 2/04541 606/167 |
| 2016/0081707 A1* | 3/2016 | Asahi | A61B 17/3203 606/167 |
| 2016/0129689 A1* | 5/2016 | Gomi | B41J 2/175 347/9 |
| 2016/0242801 A1* | 8/2016 | Gomi | B41J 2/175 |

* cited by examiner

FLUID EJECTION DEVICE

This application claims the benefit of Japanese Patent Application No. 2014-080828, filed on Apr. 10, 2014. The content of the aforementioned application is incorporated herein by reference in its entirety.

BACKGROUND

1. Technical Field

The present invention relates to a fluid ejection device.

2. Related Art

A technology in which an object is incised or excised by ejecting a pulsed fluid is known. For example, in the medical field, a fluid ejection device is proposed as an operation scalpel to incise or excise living tissue, the fluid ejection device being configured to include a pulsation generator that ejects a pulsed fluid, a fluid supply unit that supplies a fluid to the pulsation generator, a fluid supply path that connects the fluid supply unit and the pulsation generator, and an operation switch that switches between an ejection mode and a non-ejection mode (refer to JP-A-2013-213422).

In the fluid ejection device, it is necessary to supply the fluid from the fluid supply unit to the pulsation generator at a proper pressure so as to eject the fluid from the pulsation generator at a proper intensity when the operation switch is operated. For this reason, in the fluid ejection device, a valve is provided on a fluid supply path so as to be able to open and close a channel of the fluid, and when the operation switch is not operated, the fluid is sent to the fluid supply path from the fluid supply unit in a state where the channel is closed, thereby increasing the inner fluid pressure of the fluid supply unit.

Accordingly, in a case where a connection between the valve and the fluid supply path is not properly made, there is disconnect present in the middle of the connection therebetween, the valve is in a failure state, or the like, and since it is not possible to close the fluid supply path, it may not be possible to increase the inner pressure of the fluid supply unit to a proper level of pressure.

SUMMARY

An advantage of some aspects of the invention is to provide a technology in which it is possible to detect that the fluid supply path cannot be closed.

A fluid ejection device according to an aspect of the invention includes: a fluid container that has a fluid accommodation portion for accommodating a fluid, and a fluid outlet formed in the fluid accommodation portion; a fluid pressing unit that moves in a pressing direction according to a movement command, and presses the fluid accommodation portion to cause the fluid to flow out of the fluid outlet; a connection tube, one end of which is connected to the fluid outlet; a fluid ejection unit that has a fluid intake port connected to the other end of the connection tube, and ejects in a pulsed manner the fluid taken in via the fluid intake port; a pressure detection unit that detects an inner pressure of the fluid accommodation portion; a channel opening and closing unit that opens and closes a channel of the fluid in the connection tube; a press control unit that outputs the movement command to the fluid pressing unit and controls the inner pressure of the fluid accommodation portion to approach a predetermined target pressure value, in a state where the channel is closed by the channel opening and closing unit; a movement speed acquisition unit that acquires a movement speed of the fluid pressing unit; and a channel determination unit configured to determine that the channel is not closed by the channel opening and closing unit, in a case where the movement speed of the fluid pressing unit is a predetermined speed or higher when a predetermined amount of time has elapsed after a difference between the inner pressure of the fluid accommodation portion and the target pressure value becomes less than a predetermined value.

Other features of the invention will be made apparent by the description of this specification and the accompanying drawings.

BRIEF DESCRIPTION OF THE DRAWINGS

The invention will be described with reference to the accompanying drawings, wherein like numbers reference like elements.

DESCRIPTION OF EXEMPLARY EMBODIMENTS

Outline

Figure 1:
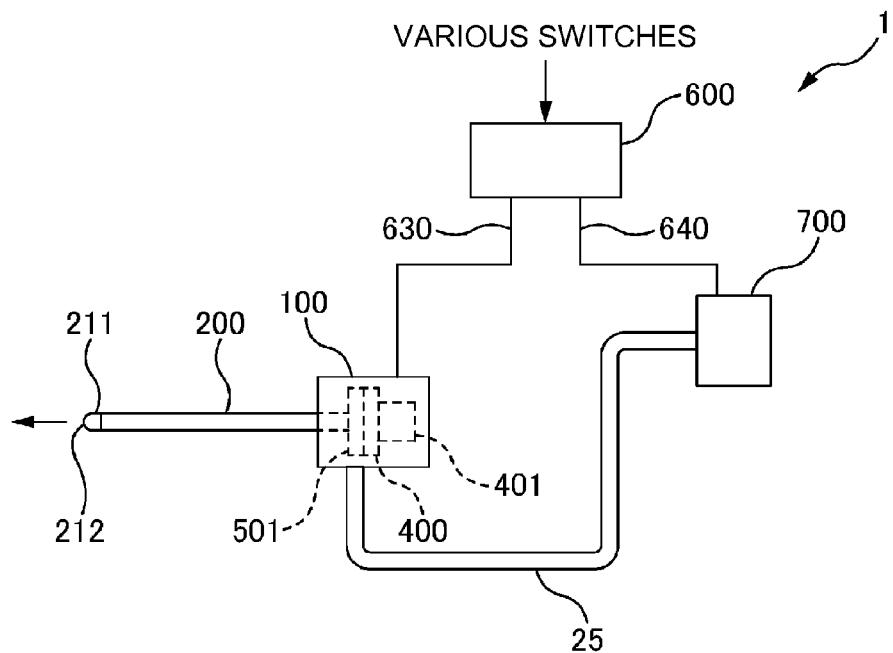
FIG. 1 is a block diagram illustrating an example of the entire configuration of a fluid ejection device according to an embodiment of the invention.

At least the following facts are apparent from this specification and the accompanying drawings.

A fluid ejection device includes: a fluid container that has a fluid accommodation portion for accommodating a fluid, and a fluid outlet formed in the fluid accommodation portion; a fluid pressing unit that moves in a pressing direction according to a movement command, and presses the fluid accommodation portion to cause the fluid to flow out of the fluid outlet; a connection tube, one end of which is connected to the fluid outlet; a fluid ejection unit that has a fluid intake port connected to the other end of the connection tube, and ejects in a pulsed manner the fluid taken in via the fluid intake port; a pressure detection unit that detects an inner pressure of the fluid accommodation portion; a channel opening and closing unit that opens and closes a channel of the fluid in the connection tube; a press control unit that outputs the movement command to the fluid pressing unit and controls the inner pressure of the fluid accommodation portion to approach a predetermined target pressure value, in a state where the channel is closed by the channel opening and closing unit; a movement speed acquisition unit that acquires a movement speed of the fluid pressing unit; and a channel determination unit configured to determine that the channel is not closed by the channel opening and closing unit, in a case where the movement speed of the fluid pressing unit is a predetermined speed or higher when a predetermined amount of time has elapsed after a difference between the inner pressure of the fluid accommodation portion and the target pressure value becomes less than a predetermined value.

The fluid ejection device with this configuration can detect that the channel of the fluid cannot be closed. Accordingly, it is possible to improve the user-friendliness and the safety of the fluid ejection device.

In the fluid ejection device, it is preferable that the movement command output from the press control unit contains distance information that specifies a movement distance of the fluid pressing unit, and the movement speed acquisition unit calculates the movement speed of the fluid pressing unit by summing up the values of the distance information contained in one or more movement commands that the press control unit outputs during a unit time.

The fluid ejection device with this configuration can detect the movement speed of the fluid pressing unit without using an encoder.

In the fluid ejection device, it is preferable that, when it is determined that the channel is not closed by the channel opening and closing unit, the press control unit stops the fluid pressing unit.

The fluid ejection device with this configuration can stop the leakage of the fluid from the fluid ejection unit.

In the fluid ejection device, it is preferable that, when it is determined that the channel is not closed by the channel opening and closing unit, the channel determination unit outputs a predetermined alarm.

The fluid ejection device with this configuration can promptly notify a practitioner that the channel is not closed, and it is possible to improve the safety of the fluid ejection device.

Entire Configuration

Hereinafter, an embodiment of the invention will be described with reference to the accompanying drawings. A fluid ejection device according to the embodiment can be used in various procedures such as the cleaning or cutting of a fine object or structure, living tissue, or the like; however, an example of the embodiment given in the following description is the fluid ejection device suitable for use as an operation scalpel to incise or excise living tissue. Accordingly, a fluid used in the fluid ejecting device according to the embodiment is water, physiologic saline, a predetermined fluid medicine, or the like. The drawings referenced in the following description are schematic views in which a portion not being as defined a member is vertically and horizontally scaled differently from an actual scale for illustrative purposes.

FIG. 1 is a view illustrating the configuration of a fluid ejection device 1 as an operation scalpel according to the embodiment. The fluid ejection device 1 according to the embodiment includes a pump 700 for supplying a fluid; a pulsation generator (a fluid ejection unit) 100 that converts a flow of the fluid supplied from the pump 700 into a pulsed flow, and ejects the fluid in a pulsed manner; a drive control unit 600 that controls the fluid ejection device 1 in cooperation with the pump 700; and a connection tube (connection path) 25 acting as a channel through which the pump 700 and the pulsation generator 100 are connected to each other, and the fluid flows.

The pulsation generator 100 includes a fluid chamber 501 that accommodates the fluid supplied from the pump 700; a diaphragm 400 that changes the volume of the fluid chamber 501; and a piezoelectric element 401 that vibrates the diaphragm 400, all of which will be described later in detail.

The pulsation generator 100 includes a thin pipe-like fluid ejection tube 200 that acts as a channel of the fluid discharged from the fluid chamber 501, and a nozzle 211 that is mounted on a tip end portion of the fluid ejection tube 200 and has a reduced channel diameter.

The pulsation generator 100 converts a flow of the fluid into a pulsed flow by applying a pulsed pressure to the fluid via the driving of the piezoelectric element 401 in response to drive signals output from the drive control unit 600 and the changing of the volume of the fluid chamber 501, and the pulsation generator 100 ejects the fluid at a high speed in a pulsed manner via the fluid ejection tube 200 and the nozzle 211.

The drive control unit 600 and the pulsation generator 100 are connected to each other via a control cable 630, and drive signals for driving the piezoelectric element 401 are output from the drive control unit 600, and are transmitted to the pulsation generator 100 via the control cable 630.

The drive control unit 600 and the pump 700 are connected to each other via a communication cable 640, and the drive control unit 600 and the pump 700 transmit and receive various commands or data therebetween according to a predetermined communication protocol such as a controller area network (CAN).

The drive control unit 600 receives signals from various switches operated by a practitioner who performs an operation using the pulsation generator 100, and controls the pump 700 or the pulsation generator 100 via the control cable 630 or the communication cable 640.

The switches that input signals to the drive control unit 600 are a pulsation generator start-up switch 625, an ejection intensity switching switch 627, a flushing switch 628, and the like (not illustrated).

The pulsation generator start-up switch 625 is a switch for switching between the ejection and the non-ejection of the fluid from the pulsation generator 100. When a practitioner who performs an operation using the pulsation generator 100 operates the pulsation generator start-up switch 625, the drive control unit 600 controls the pulsation generator 100 to eject the fluid or stop the ejection of the fluid in cooperation with the pump 700. The pulsation generator start-up switch 625 can be a switch configured to be operated by the practitioner's feet, or a switch that is provided integrally with the pulsation generator 100 grasped by the practitioner, and configured to be operated by the practitioner's hands or fingers.

The ejection intensity switching switch 627 is a switch for setting the intensity of fluid ejection from the pulsation generator 100. When the ejection intensity switching switch 627 is operated, the drive control unit 600 controls the pulsation generator 100 and the pump 700 so as to increase and decrease the intensity of fluid ejection.

For example, when the fluid is ejected from the pulsation generator 100, the drive control unit 600 outputs a voltage of a drive signal to the pulsation generator 100, the voltage being determined in response to the intensity of ejection set by the ejection intensity switching switch 627. For example, the drive control unit 600 increases a voltage of the drive signal when desiring to increase the intensity of ejection, and decreases a voltage of the drive signal when desiring to decrease the intensity of ejection.

When the pump 700 supplies the fluid to the pulsation generator 100, the pump 700 controls the inner fluid pressure of the pump 700 to become a pressure that corresponds to the intensity of ejection set by the ejection intensity switching switch 627. For example, the pump 700 increases the pressure of the fluid when desiring to increase the intensity of ejection, and decreases the pressure of the fluid when desiring to decrease the intensity of ejection.

The ejection intensity switching switch 627 may be a switch configured to be able to alternatively select one from a plurality of intensity levels of ejection, or a switch configured to continuously change the intensity of ejection between an upper limit value and a lower limit value of the intensity of ejection.

In addition, the intensity of ejection set by the ejection intensity switching switch 627 is determined by a certain physical quantity (for example, pressure received by a target for ejection, the amount of ejection per predetermined amount of time, a flow speed) which is an index of the intensity of ejection, and the intensity of ejection can be determined by any one of the physical quantities.

The flushing switch 628 will be described later.

In the embodiment, a pulsed flow implies a flow of a fluid, a flow direction of which is constant, and the flow rate or flow speed of which is changed periodically or non-periodically. The pulsed flow may be an intermittent flow in which the flowing and stopping of the fluid are repeated; however, since the flow rate or flow speed of the fluid is preferably changed periodically or non-periodically, the pulsed flow is not necessarily an intermittent flow.

Similarly, the ejection of a fluid in a pulsed form implies the ejection of the fluid by which the flow rate or moving speed of an ejected fluid is changed periodically or non-periodically. An example of the pulsed ejection is an intermittent ejection by which the ejection and non-ejection of a fluid are repeated; however, since the flow rate or moving speed of an ejected fluid is preferably changed periodically or non-periodically, the pulsed ejection is not necessarily an intermittent ejection.

When the driving of the pulsation generator 100 is stopped, that is, when the volume of the fluid chamber 501 is not changed, the fluid supplied from the pump 700 as a fluid supply unit at a predetermined pressure continuously flows out of the nozzle 211 via the fluid chamber 501.

Figure 2:
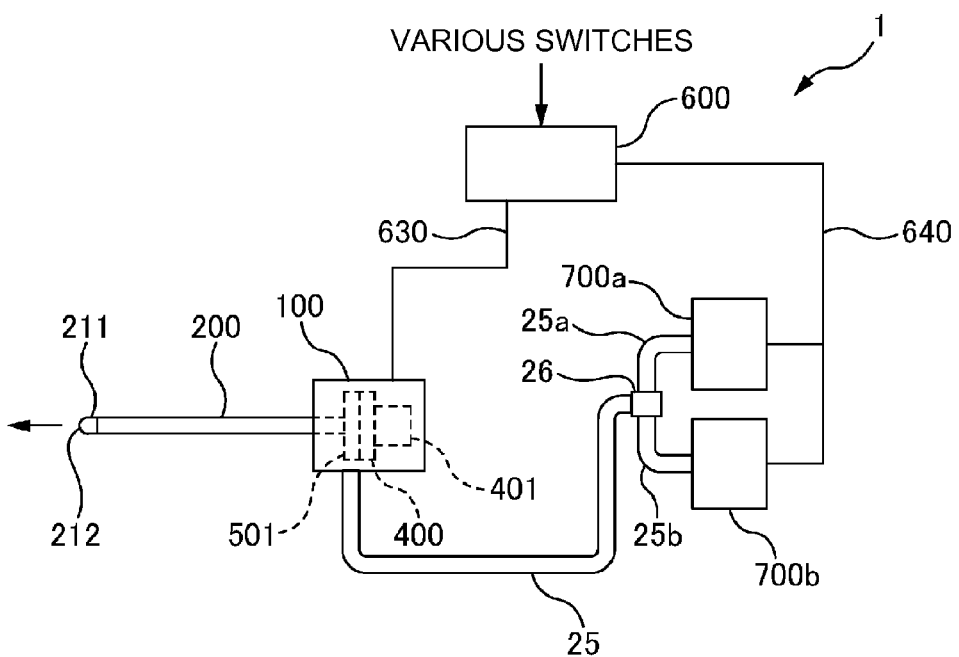
FIG. 2 is a block diagram illustrating another example of the entire configuration of the fluid ejection device according to the embodiment of the invention.

The fluid ejection device 1 according to the embodiment may be configured to include a plurality of the pumps 700. FIG. 2 illustrates an example of the configuration of the fluid ejection device 1 configured to include two pumps 700.

In this case, as illustrated in FIG. 2, the fluid ejection device 1 includes a first pump 700a and a second pump 700b. A first connection tube 25a, a second connection tube 25b, the connection tube 25, and a three way stopcock 26 form a connection path (connection tube) which connects the pulsation generator 100 and the first pump 700a, and the pulsation generator 100 and the second pump 700b, and acts as a channel through which the fluid flows.

The three way stopcock 26 is a valve configured to be able to communicate the first connection tube 25a and the connection tube 25, or the second connection tube 25b and the connection tube 25, and either one of the first pump 700a and the second pump 700b is selectively used.

In this configuration, for example, when the first pump 700a cannot supply the fluid for unknown reasons such as a malfunction while being selected and used, it is possible to continuously use the fluid ejection device 1 and to minimize adverse effects associated with the non-supply of the fluid from the first pump 700a by switching the three way stopcock 26 so as to communicate the second connection tube 25b and the connection tube 25, and starting the supply of the fluid from the second pump 700b.

When the fluid ejection device 1 is configured to include a plurality of the pumps 700, but the pumps 700 are not required to be distinctively described, in the following description, the pumps 700 are collectively expressed by the pump 700.

In contrast, when the plurality of pumps 700 are required to be distinctively described, suffixes such as "a" and "b" are properly added to reference sign 700 of the pump, and each of the pumps 700 is distinctively expressed by the first pump 700a or the second pump 700b. In this case, each configuration element of the first pump 700a is expressed by adding the suffix "a" to a reference sign of each configuration element, and each configuration element of the second pump 700b is expressed by adding the suffix "b" to a reference sign of each configuration element.

Pump

Subsequently, an outline of the configuration and operation of the pump 700 according to the embodiment will be described with reference to FIG. 3.

The pump 700 according to the embodiment includes a pump control unit (a press control unit) 710; a slider 720; a motor 730; a linear guide 740; and a pinch valve (a channel opening and closing unit) 750. The pump 700 is configured to have a fluid container mounting unit 770 for attachably and detachably mounting a fluid container 760 that accommodates the fluid. The fluid container mounting unit 770 is formed so as to hold the fluid container 760 at a specific position when the fluid container 760 is mounted thereon.

The following switches (which will be described later in detail) (not illustrated) input signals to the pump control unit 710: a slider release switch 780; a slider set switch 781; a fluid supply ready switch 782; a priming switch 783; and a pinch valve switch 785.

In the embodiment, for example, the fluid container 760 is formed of a medical syringe configured to include a syringe 761 and a plunger 762.

In the fluid container 760, a protrusive cylinder-shaped opening (a fluid outlet) 764 is formed in a tip end portion of the syringe 761. When the fluid container 760 is mounted on the fluid container mounting unit 770, an end portion of the connection tube 25 is inserted into the opening 764, and a fluid channel is formed from the inside of the syringe 761 to the connection tube 25.

The connection tube 25 is mounted on the pinch valve 750.

The pinch valve 750 is a valve that opens and closes a fluid channel between the fluid container 760 and the pulsation generator 100. The pinch valve 750 closes the fluid channel by clamping side surfaces of the connection tube 25 on both sides.

The pump control unit 710 controls the opening and closing of the pinch valve 750. When the pump control unit 710 opens the pinch valve 750, the fluid container 760 and the pulsation generator 100 communicate with each other via the channel therebetween. When the pump control unit 710 closes the pinch valve 750, the channel between the fluid container 760 and the pulsation generator 100 is shut off.

In a state where the fluid container 760 is mounted on the fluid container mounting unit 770, and the pinch valve 750 is opened, when the plunger 762 of the fluid container 760 moves in a direction (hereinafter, also referred to as a push-in direction) in which the plunger 762 is pushed into the syringe 761, the volume of a space (hereinafter, also referred to as a fluid accommodation portion 765) is reduced, the space being enveloped by an end surface of a gasket 763 made of resin such as elastic rubber and mounted at the tip of the plunger 762 in the push-in direction, and an inner wall of the syringe 761, and the fluid in the fluid accommodation portion 765 is discharged via the opening 764 of the tip end portion of the syringe 761. The connection tube 25 is filled with the fluid discharged via the opening 764, and the discharged fluid is supplied to the pulsation generator 100.

In contrast, in a state where the fluid container 760 is mounted on the fluid container mounting unit 770, and the pinch valve 750 is closed, when the plunger 762 of the fluid container 760 moves in the push-in direction, it is possible to reduce the volume of the fluid accommodation portion 765, the fluid accommodation portion 765 being enveloped by the gasket 763 mounted at the tip of the plunger 762 and the inner wall of the syringe 761, and it is possible to increase the pressure of the fluid in the fluid accommodation portion 765.

The pump control unit 710 moves the slider 720 along a direction (in the push-in direction and the opposite direction of the push-in direction) in which the plunger 762 moves in a state where the fluid container 760 is mounted on the fluid container mounting unit 770, and the plunger 762 moves in accordance with the movement of the slider 720.

Specifically, the slider 720 is attached to the linear guide 740 in such a manner that a pedestal 721 of the slider 720 engages with a rail (not illustrated) formed linearly on the linear guide 740 along the slide direction of the plunger 762. The linear guide 740 moves the pedestal 721 of the slider 720 along the rail using power transmitted from the motor 730 driven by the pump control unit 710, and thereby the slider 720 moves along the slide direction of the plunger 762.

Figure 3:
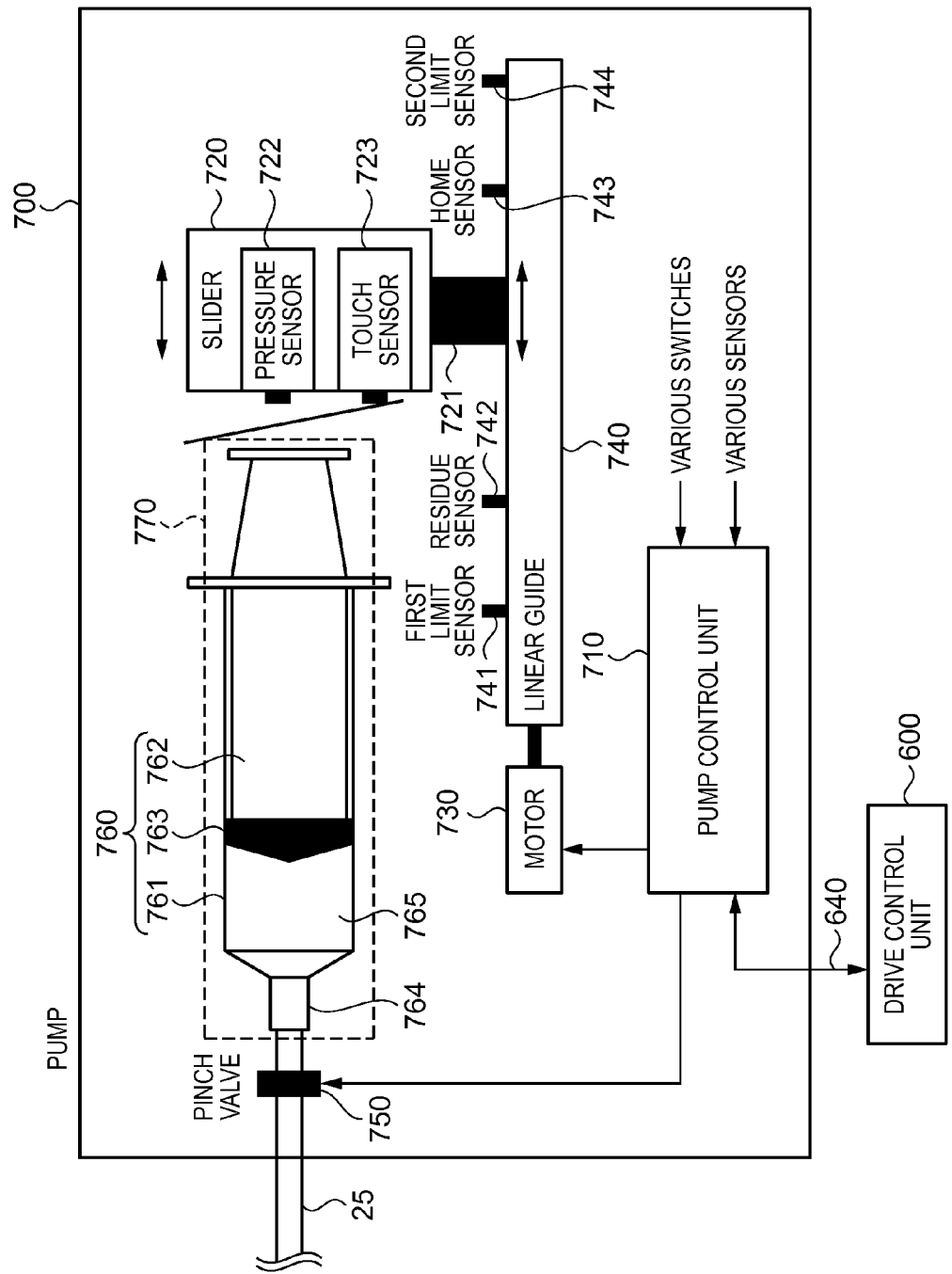
FIG. 3 is a block diagram illustrating the configuration of a pump according to the embodiment of the invention.

As illustrated in FIG. 3, the following sensors are provided along the rail of the linear guide 740: a first limit sensor 741; a residue sensor 742; a home sensor 743; and a second limit sensor 744.

All of the first limit sensor 741, the residue sensor 742, the home sensor 743, and the second limit sensor 744 are sensors for detecting the position of the slider 720 that moves on the rail of the linear guide 740, and signals detected by these sensors are input to the pump control unit 710.

The home sensor 743 is a sensor used to determine an initial position (hereinafter, also referred to as a home position) of the slider 720 on the linear guide 740. The home position is a position in which the slider 720 is held when the fluid container 760 is mounted or replaced.

The residue sensor 742 is a sensor for detecting the position (hereinafter, also referred to as a residual position) of the slider 720 when the residue of the fluid in the fluid container 760 is less than or equal to a predetermined value while the slider 720 moves from the home position in the push-in direction of the plunger 762. When the slider 720 reaches the residual position in which the residue sensor 742 is provided, a predetermined alarm is output to an operator (a practitioner or an assistant). The fluid container 760 currently in use is replaced with a new fluid container 760 at an appropriate time determined by the operator. Alternatively, when an auxiliary second pump 700b having the same configuration as that of the pump 700 (the first pump 700a) is prepared, a switching operation is performed so as to supply the fluid from the auxiliary second pump 700b to the pulsation generator 100.

The first limit sensor 741 indicates a limit position (hereinafter, referred to as a first limit position) in a movable range in which the slider 720 can move from the home position in the push-in direction of the plunger 762. When the slider 720 reaches the first limit position in which the first limit sensor 741 is provided, the residue of the fluid in the fluid container 760 is much less than the residue indicating that the slider 720 is present at the residual position, and a predetermined alarm is output to the operator. In this case, the fluid container 760 currently in use is also replaced with a new fluid container 760, or a switching operation is also performed so as to supply the fluid from an auxiliary second pump 700b.

In contrast, the second limit sensor 744 indicates a limit position (hereinafter, also referred to as a second limit position) in a movable range in which the slider 720 can move from the home position in the opposite direction of the push-in direction of the plunger 762. When the slider 720 reaches the second limit position in which the second limit sensor 744 is provided, a predetermined alarm is output.

A touch sensor 723 and a pressure sensor (a pressure detection unit) 722 are mounted on the slider 720.

The touch sensor 723 is a sensor for detecting whether the slider 720 is in contact with the plunger 762 of the fluid container 760.

The pressure sensor 722 is a sensor that detects the pressure of the fluid in the fluid accommodation portion 765 formed by the inner wall of the syringe 761 and the gasket 763, that is, a pressure when the slider 720 presses the fluid accommodation portion 765, and outputs signals (detection signals) at a level (for example, a voltage, or a voltage and a frequency) that corresponds to a detected pressure.

When the pinch valve 750 is closed, and the slider 720 moves in the push-in direction, and after the slider 720 comes into contact with the plunger 762, the pressure of the fluid in the fluid accommodation portion 765 increases to the extent that the slider 720 moves further in the push-in direction.

In contrast, when the pinch valve 750 is opened, and the slider 720 moves in the push-in direction, and even after the slider 720 comes into contact with the plunger 762, the fluid in the fluid accommodation portion 765 flows out of the nozzle 211 of the pulsation generator 100 via the connection tube 25, and thereby the pressure of the fluid in the fluid accommodation portion 765 increases to a certain level, but the pressure of the fluid does not increase even though the slider 720 moves further in the push-in direction.

The touch sensor 723 and the pressure sensor 722 input signals to the pump control unit 710.

In the following description, the slider 720, the motor 730, and the linear guide 740 may be referred to as a fluid pressing unit 731. The fluid pressing unit 731 causes the fluid to flow out of the opening (the fluid outlet) 764 of the fluid container 760 by moving the fluid accommodation portion 765 in a pressing direction, and pressing the fluid accommodation portion 765.

A description to be given hereinafter is regarding a preparation operation configured to include a process of mounting a fluid container 760 filled with the fluid on the fluid container mounting unit 770; a process of supplying the fluid in the fluid container 760 to the pulsation generator 100; and a process of bringing the fluid ejection device 1 into a state in which the pulsation generator 100 can eject the fluid in the form of a pulsed flow.

First, the operator inputs an ON signal of the slider release switch 780 to the pump control unit 710 by operating the slider release switch 780. Thus, the pump control unit 710 moves the slider 720 to the home position.

The operator mounts the fluid container 760 connected to the connection tube 25 in advance on the fluid container mounting unit 770. The syringe 761 of the fluid container 760 is already filled with the fluid.

When the operator sets the connection tube 25 to the pinch valve 750, and then inputs an ON signal of the pinch valve switch 785 to the pump control unit 710 by operating the pinch valve switch 785, the pump control unit 710 closes the pinch valve 750.

Subsequently, the operator inputs an ON signal of the slider set switch 781 to the pump control unit 710 by operating the slider set switch 781. Thus, the pump control unit 710 starts a control operation in such a manner that the slider 720 moves in the push-in direction and the pressure of the fluid accommodated in the fluid accommodation portion 765 of the fluid container 760 becomes a predetermined target pressure value that is determined corresponding to the intensity of ejection set by the ejection intensity switching switch 627.

Thereafter, when the operator inputs an ON signal of the fluid supply ready switch 782 to the pump control unit 710 by pushing the fluid supply ready switch 782, and the pressure of the fluid in the fluid accommodation portion 765 enters a specific range (hereinafter, also referred to as a rough window) for the target pressure value, the pump control unit 710 is brought into a fluid suppliable state in which the fluid is allowed to be supplied from the pump 700 to the pulsation generator 100.

When the pump control unit 710 is in a fluid suppliable state, and the operator inputs an ON signal of the priming switch 783 to the pump control unit 710 by operating the priming switch 783, the pump control unit 710 starts a priming process. The priming process is a process by which a fluid channel from the fluid container 760 to the connection tube 25 and to a fluid ejection opening 212 of the pulsation generator 100 is filled up with the fluid.

When the priming process starts, the pump control unit 710 opens the pinch valve 750, and starts moving the slider 720 in the push-in direction at the same time or substantially the same time (for example, a time gap of approximately several milliseconds or approximately several tens of milliseconds) as when the pinch valve 750 is opened. The slider 720 moves at a predetermined speed in such a manner that a constant amount of the fluid per unit time is supplied from the fluid container 760. The priming process is performed until a predetermined amount of time required to complete the priming process has elapsed (or the slider 720 moves by a predetermined distance), or the operator inputs an OFF signal of the priming switch 783 by operating the priming switch 783.

Accordingly, a predetermined amount of the fluid in the fluid accommodation portion 765 is supplied at a predetermined flow speed (the amount of discharge of the fluid per unit time) from the pump 700, the connection tube 25 from the pinch valve 750 to the pulsation generator 100 is filled up with the fluid, and the fluid chamber 501 of the pulsation generator 100, the fluid ejection tube 200 and the like are filled up with the fluid. Air present in the connection tube 25 or the pulsation generator 100 prior to the start of the priming process is released to the atmosphere via the nozzle 211 of the pulsation generator 100 as the fluid flows into the connection tube 25 or the pulsation generator 100.

The pump control unit 710 pre-stores the predetermined speed, the predetermined distance, and the predetermined amount of time in relation to the movement of the slider 720 during the priming process.

As such, the priming process is completed.

Subsequently, when the operator inputs an ON signal of the flushing switch 628 to the drive control unit 600 by operating the flushing switch 628, the drive control unit 600 and the pump control unit 710 start a deaeration process.

The deaeration process is a process by which air bubbles remaining in the connection tube 25 or the pulsation generator 100 are discharged via the nozzle 211 of the pulsation generator 100.

In the deaeration process, in a state in which the pinch valve 750 is opened, the pump control unit 710 moves the slider 720 in the push-in direction at the predetermined speed in such a manner that a constant amount of the fluid per unit time is supplied from the fluid container 760, and the fluid is supplied to the pulsation generator 100. The drive control unit 600 drives the piezoelectric element 401 of the pulsation generator 100 in conjunction with the discharge of the fluid by the pump 700, and thereby the pulsation generator 100 to eject the fluid. Accordingly, air bubbles remaining in the connection tube 25 or the pulsation generator 100 are discharged via the nozzle 211 of the pulsation generator 100. The deaeration process is performed until a predetermined amount of time has elapsed (or the slider 720 moves by a predetermined distance), or the operator inputs an OFF signal of the flushing switch 628 by operating the flushing switch 628.

The drive control unit 600 and the pump control unit 710 pre-store the predetermined speed, the predetermined distance, and the predetermined amount of time in relation to the movement of the slider 720 during the deaeration process.

When the deaeration process is completed, the pump control unit 710 closes the pinch valve 750, and detects the pressure of the fluid accommodated in the fluid accommodation portion 765 of the fluid container 760. The pump control unit 710 performs a control operation in which the position of the slider 720 is adjusted in order for the pressure to become the target pressure value determined corresponding to the intensity of ejection.

Thereafter, when the pressure of the fluid in the fluid accommodation portion 765 enters a specific range (a rough window) for the target pressure value, the pump control unit 710 is brought into a fluid ejectable state in which the fluid can be ejected in the form of a pulsed flow from the pulsation generator 100.

In this state, when the operator inputs an ON signal of the pulsation generator start-up switch 625 to the drive control unit 600 by operating the pulsation generator start-up switch 625 via the feet, the pump control unit 710 opens the pinch valve 750 in response to signals transmitted from the drive control unit 600, and starts the supply of the fluid to the pulsation generator 100 by moving the slider 720 at a predetermined speed in the push-in direction at the same time or substantially the same time (for example, a time gap of approximately several milliseconds or approximately several tens of milliseconds) as when the pinch valve 750 is opened. In contrast, the drive control unit 600 generates a pulsed flow by starting the driving of the piezoelectric element 401 and changing the volume of the fluid chamber 501. Accordingly, a pulsed flow of the fluid is ejected at a high speed via the nozzle 211 at the tip of the pulsation generator 100.

Thereafter, when the operator inputs an OFF signal of the pulsation generator start-up switch 625 to the drive control unit 600 by operating the pulsation generator start-up switch 625 via the feet, the drive control unit 600 stops the driving of the piezoelectric element 401. The pump control unit 710 stops the movement of the slider 720 in response to signals transmitted from the drive control unit 600, and closes the pinch valve 750. As such, the pulsation generator 100 stops the ejection of the fluid.

In addition, in the embodiment, the drive control unit 600 is provided separately from the pump 700 and the pulsation generator 100; however, the drive control unit 600 may be provided integrally with the pump 700.

When the practitioner performs an operation using the fluid ejection device 1, the practitioner grasps the pulsation generator 100. Accordingly, the connection tube 25 up to the pulsation generator 100 is preferably as flexible as possible. For this reason, a flexible thin tube is used as the connection tube 25, and a fluid discharge pressure of the pump 700 is preferably set to a low pressure in a pressure range in which the fluid can be supplied to the pulsation generator 100. For this reason, the discharge pressure of the pump 700 is set to approximately 0.3 atm (0.03 MPa) or less.

In particular, in a case where a malfunction of an apparatus may lead to a serious accident, for example, for a brain surgery, it is necessary to prevent the cutting of the connection tube 25 from causing the ejection of the fluid at a high pressure, and also, for this reason, the discharge pressure of the pump 700 is required to be set to a low pressure.

Pulsation Generator

Subsequently, the structure of the pulsation generator 100 according to the embodiment will be described.

Figure 4:
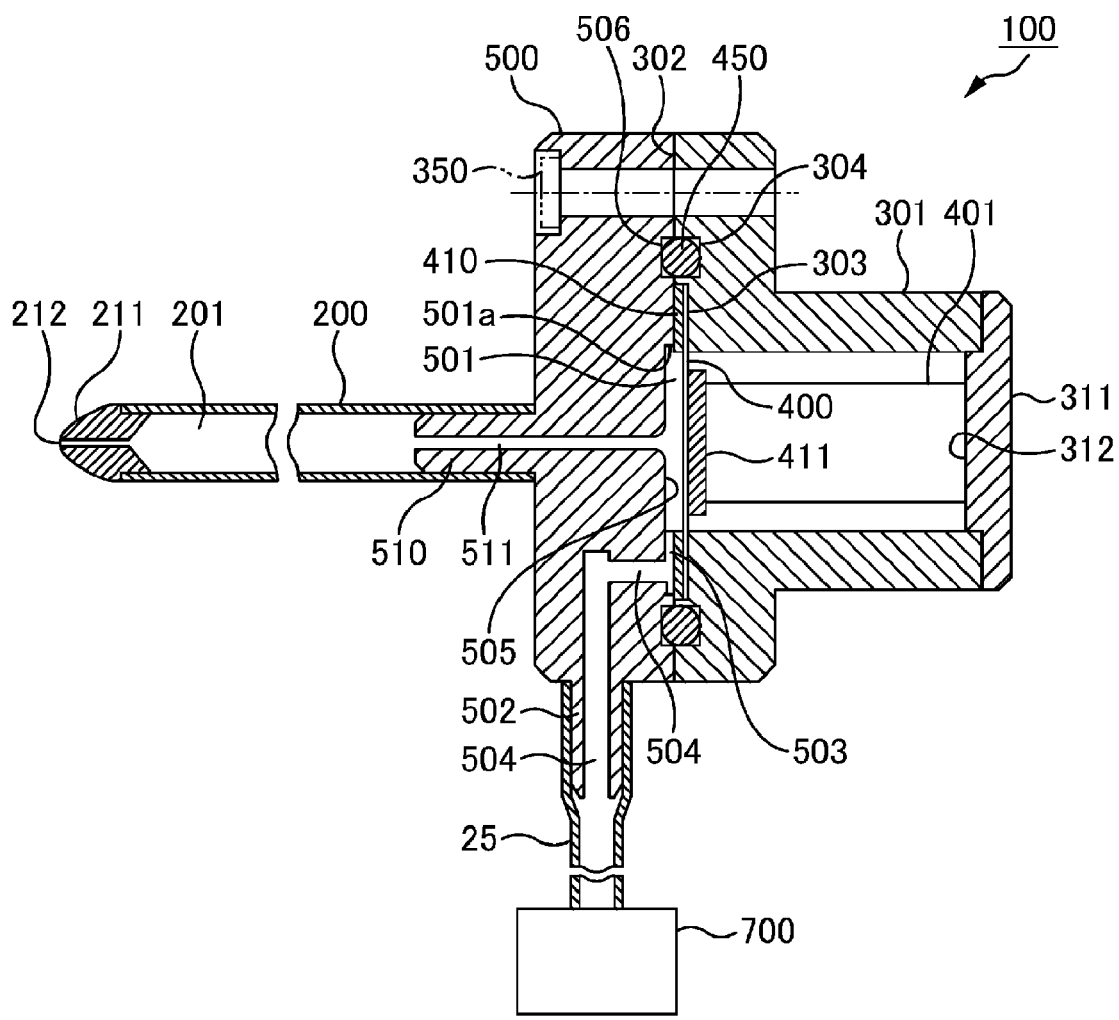
FIG. 4 is a cross-sectional view illustrating the structure of a pulsation generator according to the embodiment of the invention.

FIG. 4 is a cross-sectional view illustrating the structure of the pulsation generator 100 according to the embodiment. In FIG. 4, the pulsation generator 100 includes a pulse generation unit that generates the pulsation of the fluid, and is connected to the fluid ejection tube 200 having a connection channel 201 as a channel through which the fluid is discharged.

In the pulsation generator 100, an upper case 500 and a lower case 301 are screwed together with four fixation screws 350 (not illustrated) while the respective facing surfaces thereof are bonded to each other. The lower case 301 is a cylindrical member having a flange, and one end portion of the lower case 301 is sealed with a bottom plate 311. The piezoelectric element 401 is provided in an inner space of the lower case 301.

The piezoelectric element 401 is a stack-type piezoelectric element, and acts as an actuator. One end portion of the piezoelectric element 401 is firmly fixed to the diaphragm 400 via an upper plate 411, and the other end portion is firmly fixed to an upper surface 312 of the bottom plate 311.

The diaphragm 400 is made of a circular disc-like thin metal plate, and a circumferential edge portion of the diaphragm 400 is firmly fixed to a bottom surface of a concave portion 303 in the lower case 301 while being in close contact with the bottom surface of the concave portion 303. When drive signals are input to the piezoelectric element 401 that acts as a volume change unit, the piezoelectric element 401 changes the volume of the fluid chamber 501 via the diaphragm 400 through the extension and contraction thereof.

A reinforcement plate 410 is provided in such a manner as to be stacked on an upper surface of the diaphragm 400, and is made of a circular disc-like thin metal plate having an opening at the center thereof.

The upper case 500 has a concave portion formed in a center portion of the surface facing the lower case 301, and the fluid chamber 501 is a rotator-shaped space formed by this concave portion and the diaphragm 400 and filled with the fluid. That is, the fluid chamber 501 is a space enveloped by a sealing surface 505 and an inner side wall 501a of the concave portion of the upper case 500, and the diaphragm 400. An outlet channel 511 is drilled in an approximately center portion of the fluid chamber 501.

The outlet channel 511 passes through the outlet channel tube 510 from the fluid chamber 501 to an end portion of an outlet channel tube 510 provided in such a manner as to protrude from one end surface of the upper case 500. A connection portion between the outlet channel 511 and the sealing surface 505 of the fluid chamber 501 is smoothly rounded so as to reduce fluid resistance.

In the embodiment (refer to FIG. 4), the fluid chamber 501 has a substantially cylindrical shape having sealed opposite ends; however, the fluid chamber 501 may have a conical shape, a trapezoidal shape, a hemispherical shape, or the like in a side view, and the shape of the fluid chamber 501 is not limited to a cylindrical shape. For example, when the connection portion between the outlet channel 511 and the sealing surface 505 has a funnel shape, air bubbles in the fluid chamber 501 (to be described later) are easily discharged.

The fluid ejection tube 200 is connected to the outlet channel tube 510. The connection channel 201 is drilled in the fluid ejection tube 200, and the diameter of the connection channel 201 is larger than that of the outlet channel 511. In addition, the tube thickness of the fluid ejection tube 200 is formed so as to have a range of rigidity in which the fluid ejection tube 200 does not absorb pressure pulsation of the fluid.

The nozzle 211 is inserted into the tip end portion of the fluid ejection tube 200. A fluid ejection opening 212 is drilled in the nozzle 211. The diameter of the fluid ejection opening 212 is smaller than that of the connection channel 201.

An inlet channel tube (a fluid intake port) 502 is provided in such a manner as to protrude from a side surface of the upper case 500, and is inserted into the connection tube 25 through which the fluid is supplied from the pump 700. A connection channel 504 for the inlet channel is drilled in the inlet channel tube 502. The connection channel 504 communicates with an inlet channel 503. The inlet channel 503 is formed in a groove shape in a circumferential edge portion of the sealing surface 505 of the fluid chamber 501, and communicates with the fluid chamber 501.

A packing box 304 and a packing box 506 are respectively formed in the bonded surfaces of the lower case 301 and the upper case 500 at positions separated from an outer circumferential direction of the diaphragm 400, and a ring-shaped packing 450 is mounted in a space formed by the packing boxes 304 and 506.

Here, when the upper case 500 and the lower case 301 are assembled together, the circumferential edge portion of the diaphragm 400 is in close contact with a circumferential edge portion of the reinforcement plate 410 due to the circumferential edge portion of the sealing surface 505 of the upper case 500 and the bottom surface of the concave portion 303 of the lower case 301. At this time, the packing 450 is pressed by the upper case 500 and the lowercase 301, and thereby the fluid is prevented from leaking from the fluid chamber 501.

Since the inner pressure of the fluid chamber 501 becomes a high pressure of 30 atm (3 MPa) or greater during the discharge of the fluid, the fluid may slightly leak from the respective connections between the diaphragm 400, the reinforcement plate 410, the upper case 500, and the lower case 301; however, the leakage of the fluid is prevented due to the packing 450.

As illustrated in FIG. 4, in the case where the packing 450 is provided, since the packing 450 is compressed due to the pressure of the fluid leaking from the fluid chamber 501 at a high pressure, and is strongly pressed against the respective walls of the packing boxes 304 and 506, it is possible to more reliably prevent the leakage of the fluid. For this reason, it is possible to maintain a considerable increase in the inner pressure of the fluid chamber 501 during the driving of the pulsation generator 100.

Subsequently, the inlet channel 503 formed in the upper case 500 will be described with reference to the drawings in more detail.

Figure 5:
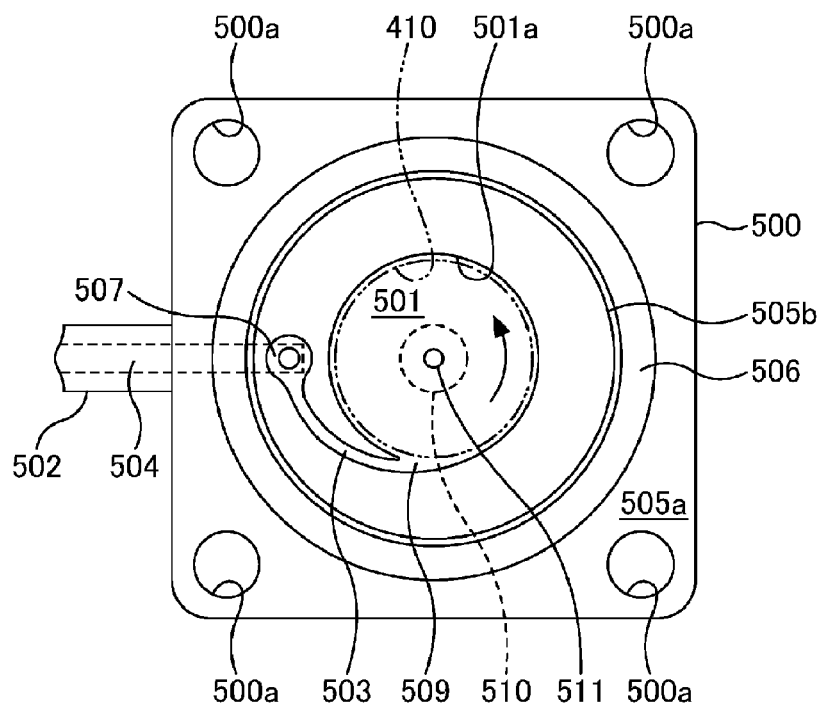
FIG. 5 is a plan view illustrating the shape of an inlet channel according to the embodiment of the invention.

FIG. 5 is a plan view illustrating the shape of the inlet channel 503, and FIG. 5 illustrates the shape of the upper case 500 when the surface of the upper case 500 bonded to the lower case 301 is seen.

In FIG. 5, the inlet channel 503 is formed in a groove shape in the circumferential edge portion of the sealing surface 505 of the upper case 500.

One end portion of the inlet channel 503 communicates with the fluid chamber 501, and the other end portion communicates with the connection channel 504. A fluid sump 507 is formed in a connection portion between the inlet channel 503 and the connection channel 504. A connection portion between the fluid sump 507 and the inlet channel 503 is smoothly rounded, and thereby fluid resistance is reduced.

The inlet channel 503 communicates with the fluid chamber 501 in a substantially tangential direction with respect to an inner circumferential side wall 501a of the fluid chamber 501. The fluid supplied from the pump 700 (refer to FIG. 1) at a predetermined pressure flows along the inner circumferential side wall 501a (in a direction illustrated by the arrow in FIG. 5), and generates a swirl flow in the fluid chamber 501. The swirl flow is pushed against the inner circumferential side wall 501a due to a centrifugal force associated with the swirling of the fluid, and air bubbles in the fluid chamber 501 are concentrated in a center portion of the swirl flow.

The air bubbles concentrated in the center portion are discharged via the outlet channel 511. For this reason, the outlet channel 511 is preferably provided in the vicinity of the center of the swirl flow, that is, in an axial center portion of a rotor shape.

As illustrated in FIG. 5, the inlet channel 503 is curved. The inlet channel 503 may communicate with the fluid chamber 501 while not being curved but being linearly formed; however, when the inlet channel 503 is curved, a channel length is increased, and a desired inertance (to be described later) is obtained in a small space.

As illustrated in FIG. 5, the reinforcement plate 410 is provided between the diaphragm 400 and the circumferential edge portion of the sealing surface 505, in which the inlet channel 503 is formed. The reinforcement plate 410 is provided so as to improve the durability of the diaphragm 400. Since a cut-out connection opening 509 is formed in a connection portion between the inlet channel 503 and the fluid chamber 501, when the diaphragm 400 is driven at a high frequency, stress may be concentrated in the vicinity of the connection opening 509, and thereby a fatigue failure may occur in the vicinity of the connection opening 509. It is possible to prevent stress from being concentrated on the diaphragm. 400 by providing the reinforcement plate 410 with an opening not having a cut-out portion and being continuously formed.

Four screw holes 500a are respectively provided in outer circumferential corner portions of the upper case 500, and the upper case 500 and the lower case 301 are bonded to each other via screwing at the positions of the screw holes.

It is possible to firmly fix the reinforcement plate 410 and the diaphragm 400 in an integrally stacked state by bonding together the reinforcement plate 410 and the diaphragm 400, which is not illustrated. An adhesive method using an adhesive, a solid-state diffusion bonding method, a welding method, or the like may be used so as to firmly fix together the reinforcement plate 410 and the diaphragm 400; however, the respective bonded surfaces of the reinforcement plate 410 and the diaphragm 400 are preferably in close contact with each other.

Operation of Pulsation Generator

Subsequently, an operation of the pulsation generator 100 according to the embodiment will be described with reference to FIGS. 1 to 5. The pulsation generator 100 according to the embodiment discharges the fluid due to a difference between an inertance L1 (may be referred to as a combined inertance L1) of the inlet channel 503 and the peripherals and an inertance L2 (may be referred to as a combined inertance L2) of the outlet channel 511 and the peripherals.

Inertance

First, the inertance will be described.

An inertance L is expressed by $L=\rho \times h/S$, and here, $\rho$ is the density of a fluid, S is the cross-sectional area of a channel, and h is a channel length. When $\Delta P$ is a differential pressure of the channel, and Q is a flow rate of the fluid flowing through the channel, it is possible to deduce a relationship $\Delta P=L \times dQ/dt$ by modifying an equation of motion in the channel using the inertance L.

That is, the inertance L indicates a degree of influence on a change in flow rate with time, and a change in flow rate with time decreases to the extent that the inertance L is large, and a change in flow rate with time increases to the extent that the inertance L is small.

Similar to a parallel connection or a series connection of inductances in an electric circuit, it is possible to calculate a combined inertance with respect to a parallel connection of a plurality of channels or a series connection of a plurality of channels having different shapes by combining an inertance of each of the channels.

Since the diameter of the connection channel 504 is set to be larger much than that of the inlet channel 503, the inertance L1 of the inlet channel 503 and the peripherals can be calculated from a boundary of the inlet channel 503. At this time, since the connection tube 25 that connects the pump 700 and the inlet channel 503 is flexible, the connection tube 25 may not be taken into consideration in calculating the inertance L1.

Since the diameter of the connection channel 201 is larger much than that of the outlet channel 511, and the tube (tube wall) thickness of the fluid ejection tube 200 is thin, the connection tube 25 and the fluid ejection device 1 have a negligible influence on the inertance L2 of the outlet channel 511 and the peripherals. Accordingly, the inertance L2 of the outlet channel 511 and the peripherals may be replaced with an inertance of the outlet channel 511.

The rigidity of the tube wall thickness of the fluid ejection tube 200 is sufficient to propagate the pressure of the fluid.

In the embodiment, a channel length and a cross-sectional area of the inlet channel 503 and a channel length and a cross-sectional area of the outlet channel 511 are set in such a manner that the inertance L1 of the inlet channel 503 and the peripherals is greater than the inertance L2 of the outlet channel 511 and the peripherals.

Ejection of Fluid

Subsequently, an operation of the pulsation generator 100 will be described.

The pump 700 supplies the fluid to the inlet channel 503 at a predetermined pressure. As a result, when the piezoelectric element 401 is not operated, the fluid flows into the fluid chamber 501 due to a difference between a discharge force of the pump 700 and a fluid resistance value for the entirety of the inlet channel 503 and the peripherals.

Here, in a case where the inertance L1 of the inlet channel 503 and the peripherals and the inertance L2 of the outlet channel 511 and the peripherals are considerably large, when a drive signal is input to the piezoelectric element 401, and the piezoelectric element 401 extends rapidly, the inner pressure of the fluid chamber 501 increases rapidly, and reaches several tens of atmosphere.

Since the inner pressure of the fluid chamber 501 is larger much than the pressure applied to the inlet channel 503 by the pump 700, the flow of the fluid from the inlet channel 503 to the fluid chamber 501 decreases due to the pressure, and the flow of the fluid out of the outlet channel 511 increases.

Since the inertance L1 of the inlet channel 503 is larger than the inertance L2 of the outlet channel 511, an increase in a flow rate of the fluid discharged from the outlet channel 511 is larger than a decrease in a flow rate of the fluid flowing from the inlet channel 503 into the fluid chamber 501. Accordingly, the fluid is discharged in the form of a pulsed flow to the connection channel 201, that is, a pulsed flow occurs. Discharge pressure pulsation propagates in the fluid ejection tube 200, and the fluid is ejected via the fluid ejection opening 212 of the nozzle 211 at the tip end.

Here, since the diameter of the fluid ejection opening 212 of the nozzle 211 is smaller than that of the outlet channel 511, a pulsed flow of the fluid is ejected as droplets at a higher pressure and speed.

In contrast, immediately after a pressure increase, the inner pressure of the fluid chamber 501 becomes negative due to interaction between a decrease in the amount of inflow of the fluid from the inlet channel 503 and an increase in the amount of outflow of the fluid from the outlet channel 511. As a result, after a predetermined amount of time has elapsed, due to both of the pressure of the pump 700 and the negative inner pressure of the fluid chamber 501, the fluid flows from the inlet channel 503 into the fluid chamber 501 again at the same speed as that before the operation of the piezoelectric element 401.

When the piezoelectric element 401 extends after the outflow of the fluid from the inlet channel 503 is restored, it is possible to continuously eject the fluid in the form of a pulsed flow via the nozzle 211.

Discharge of Air Bubbles

Subsequently, an operation of discharging air bubbles from the fluid chamber 501 will be described.

As described above, the inlet channel 503 communicates with the fluid chamber 501 via a path that approaches the fluid chamber 501 while swirling around the fluid chamber 501. The outlet channel 511 is provided in the vicinity of a rotational axis of a substantially rotor-shaped fluid chamber 501.

For this reason, the fluid flowing from the inlet channel 503 into the fluid chamber 501 swirls along the inner circumferential side wall 501a of the fluid chamber 501. The fluid is pushed against the inner circumferential side wall 501a of the fluid chamber 501 due to a centrifugal force, and air bubbles contained in the fluid are concentrated in the center portion of the fluid chamber 501, and are discharged via the outlet channel 511.

Accordingly, even when a small amount of the volume of the fluid chamber 501 is changed in association with the operation of the piezoelectric element 401, it is possible to obtain a sufficient pressure increase while a pressure pulsation is not adversely affected by air bubbles.

In the embodiment, since the pump 700 supplies the fluid to the inlet channel 503 at a predetermined pressure, even when the driving of the pulsation generator 100 is stopped, the fluid is supplied to the inlet channel 503 and the fluid chamber 501. Accordingly, it is possible to start an initial operation without an aid of a prime operation.

Since the fluid is ejected via the fluid ejection opening 212 having a diameter smaller than that of the outlet channel 511, an inner fluid pressure is increased higher than that of the outlet channel 511, and thereby it is possible to eject the fluid at a high speed.

Since the rigidity of the fluid ejection tube 200 is sufficient to transmit a pulsation of the fluid from the fluid chamber 501 to the fluid ejection opening 212, it is possible to eject the fluid in the form of a desired pulsed flow without disturbing pressure propagation of the fluid from the pulsation generator 100.

Since the inertance of the inlet channel 503 is set to be larger than that of the outlet channel 511, an increase in the amount of outflow of the fluid from the outlet channel 511 is larger than a decrease in the amount of inflow of the fluid from the inlet channel 503 into the fluid chamber 501, and it is possible to discharge the fluid into the fluid ejection tube 200 in the form of a pulsed flow. Accordingly, a check valve is not required to be provided in the inlet channel 503, it is possible to simplify the structure of the pulsation generator 100, it is easy to clean the inside of the pulsation generator 100, and it is possible to remove a potential durability problem associated with the use of the check valve.

Since the respective inertances of both of the inlet channel 503 and the outlet channel 511 are set to be considerably large, it is possible to rapidly increase the inner pressure of the fluid chamber 501 by rapidly reducing the volume of the fluid chamber 501.

Since the piezoelectric element 401 as a volume change unit and the diaphragm 400 are configured so as to generate a pulsation, it is possible to simplify the structure of the pulsation generator 100 and to reduce the size of the pulsation generator 100 in association therewith. It is possible to set the maximum frequency of a change in the volume of the fluid chamber 501 to a high frequency of 1 KHz or greater, and the pulsation generator 100 is optimized to eject a pulsed flow of the fluid at a high speed.

In the pulsation generator 100, since the inlet channel 503 generates a swirl flow of the fluid in the fluid chamber 501, the fluid in the fluid chamber 501 is pushed in an outer circumferential direction of the fluid chamber 501 due to a centrifugal force, air bubbles contained in the fluid are concentrated in the center portion of the swirl flow, that is, in the vicinity of the axis of the substantially rotor shape, and thereby it is possible to discharge the air bubbles via the outlet channel 511 provided in the vicinity of the axis of the substantially rotor shape. For this reason, it is possible to prevent a decrease in pressure amplitude associated with the stagnation of air bubbles in the fluid chamber 501, and it is possible to continuously and stably drive the pulsation generator 100.

Since the inlet channel 503 is formed in such a manner as to communicate with the fluid chamber 501 via the path that approaches the fluid chamber 501 while swirling around the fluid chamber 501, it is possible to generate a swirl flow without adopting a structure dedicated for swirling the fluid in the fluid chamber 501.

Since the groove-shaped inlet channel 503 is formed in the outer circumferential edge portion of the sealing surface 505 of the fluid chamber 501, it is possible to form the inlet channel 503 (a swirl flow generation unit) without increasing the number of components.

Since the reinforcement plate 410 is provided on the upper surface of the diaphragm 400, the diaphragm 400 is driven with respect to an outer circumference (a fulcrum) of the opening of the reinforcement plate 410, and thereby the concentration of stress is unlikely to occur, and it is possible to improve the durability of the diaphragm 400.

When corners of the surface of the reinforcement plate 410 bonded to the diaphragm 400 are rounded, it is possible to further reduce the concentration of stress on the diaphragm 400.

When the reinforcement plate 410 and the diaphragm 400 are firmly and integrally fixed together while being stacked on each other, it is possible to improve the assemblability of the pulsation generator 100, and it is possible to reinforce the outer circumferential edge portion of the diaphragm 400.

Since the fluid sump 507 for the stagnation of the fluid is provided in the connection portion between the connection channel 504 on an inlet side for supplying the fluid from the pump 700 and the inlet channel 503, it is possible to prevent the inertance of the connection channel 504 from affecting the inlet channel 503.

In the respective bonded surfaces of the lower case 301 and the upper case 500, the ring-shaped packing 450 is provided at the position separated from the outer circumferential direction of the diaphragm 400, and thereby it is possible to prevent the leakage of the fluid from the fluid chamber 501, and to prevent a decrease in the inner pressure of the fluid chamber 501.

Non-Closeable Channel Detection Process

In the fluid ejection device 1 according to the embodiment, the inner fluid pressure of the fluid accommodation portion 765 is controlled to become the predetermined target pressure value. When the inner pressure of the fluid accommodation portion 765 enters the rough window for the target pressure value, the fluid ejection device 1 can eject the fluid from the pulsation generator 100 in a pulsed manner.

In a case where the connection tube 25 is not mounted on the pinch valve 750, the connection tube 25 is detached from the pinch valve 750, or the pinch valve 750 cannot close the connection tube 25 due to a failure, the inner pressure of the fluid accommodation portion 765 decreases because the fluid in the fluid accommodation portion 765 flows via the nozzle 211 at the tip of the pulsation generator 100 even though the pump control unit 710 controls the inner pressure of the fluid accommodation portion 765 to approach the target pressure value.

For this reason, the fluid ejection device 1 with the following configuration according to the embodiment detects whether the pinch valve 750 cannot close the fluid channel by using the following method.

In the embodiment, a non-closeable channel detection process performed by the fluid ejection device 1 will be described in detail with reference to FIGS. 6 to 10.

Figure 6:
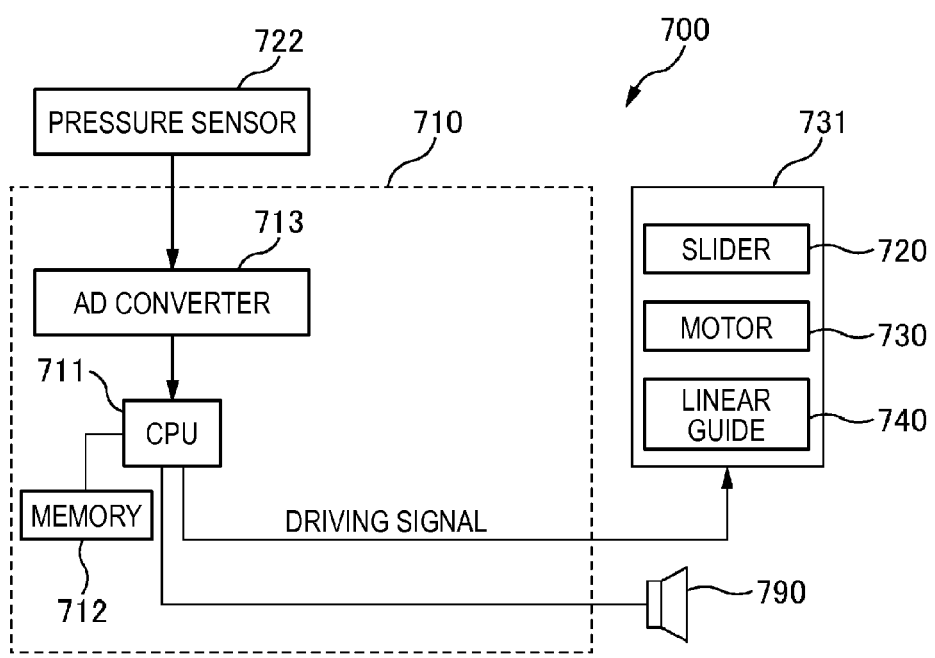
FIG. 6 is a block diagram illustrating the configuration of a pump control unit according to the embodiment of the invention.

First, the configuration of the pump control unit (the press control unit) 710 will be described with reference to FIG. 6.

The pump control unit 710 is configured to have a central processing unit (CPU) 711, a memory 712, and an analog/digital (AD) converter 713.

The pump control unit 710 takes from the pressure sensor 722 a detection signal corresponding to the inner pressure of the fluid accommodation portion 765 of the fluid container 760, and the pump control unit 710 controls the fluid pressing unit 731. For example, when the pump control unit 710 receives an ON signal of the slider set switch 781, the pump control unit 710 controls the pressure to approach the target pressure value by outputting a predetermined drive signal (a movement command) to the fluid pressing unit 731 and driving the motor 730. The fluid pressing unit 731 is configured to have the slider 720, the motor 730, and the linear guide 740.

The CPU 711 controls the entirety of the pump control unit 710, and realizes various functions of the embodiment by executing a program stored in the memory 712 and coded to perform various operations.

The memory 712 stores various pieces of data other than the program. For example, the memory 712 stores target pressure value data equivalent to the target pressure value, rough window upper limit value data equivalent to an upper limit value for the rough window, and rough window lower limit value data equivalent to a lower limit value for the rough window.

In addition, the memory 712 stores fine window upper limit value data equivalent to an upper limit value for the fine window, and fine window lower limit value data equivalent to a lower limit value for the fine window, which will be described later.

The AD converter 713 receives a detection signal output from the pressure sensor 722, and outputs data indicative of a level of the detection signal. Specifically, the pressure sensor 722 detects the inner pressure of the fluid accommodation portion 765, and outputs a level (for example, a voltage) of a detection signal corresponding to the pressure. The AD converter 713 outputs detected level data (for example, a voltage value) indicative of the level of the detection signal output from the pressure sensor 722.

The CPU 711 takes the detected level data output from the AD converter 713, and compares the detected level data with various pieces of data stored in the memory 712.

Subsequently, in the embodiment, the non-closeable channel detection process performed by the fluid ejection device 1 will be described with reference to FIGS. 7 and 8.

Figure 7:
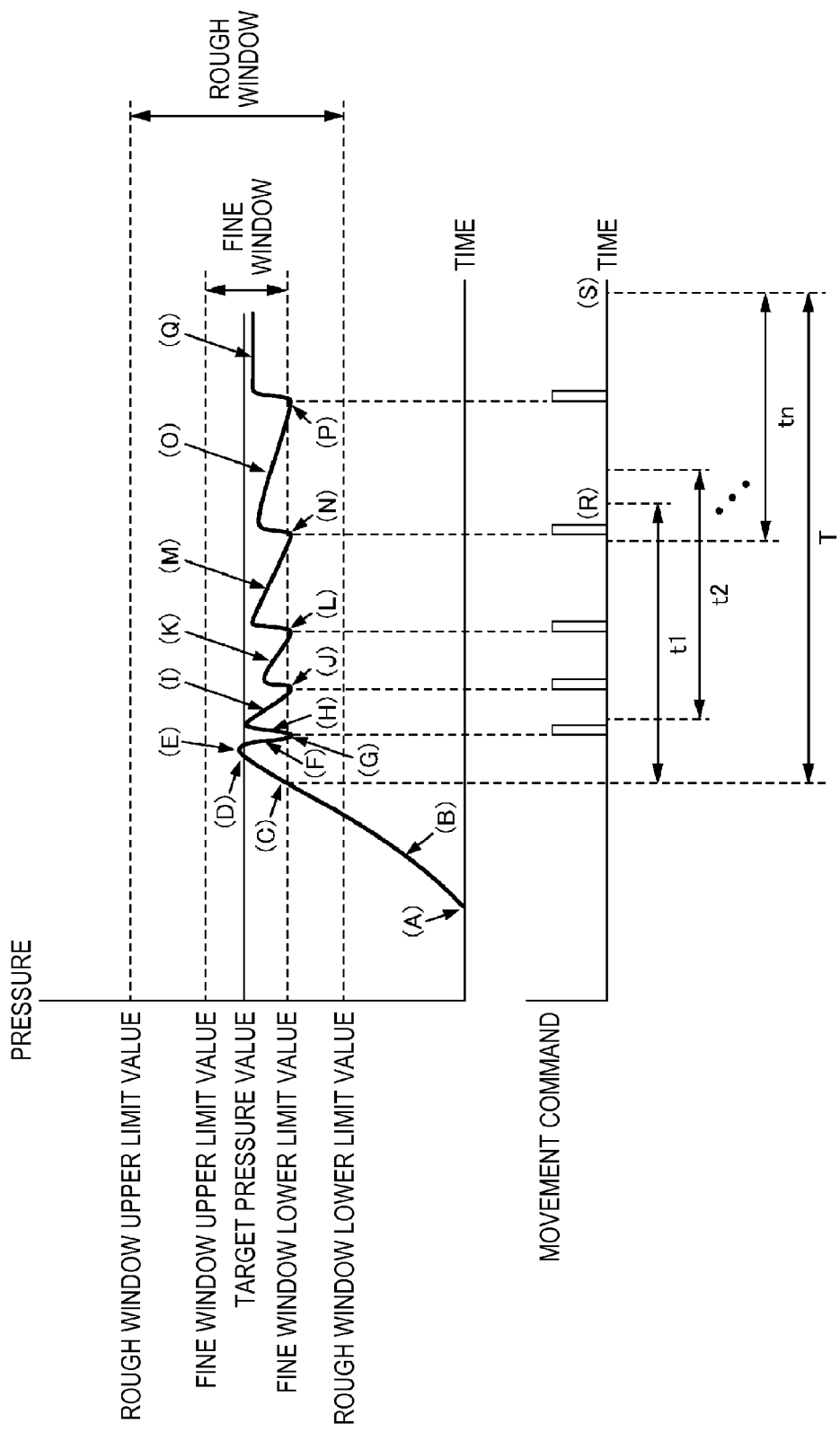
FIG. 7 is a graph illustrating a transition in the inner pressure of a fluid accommodation portion according to the embodiment of the invention.

FIG. 7 is a graph illustrating an example when the pump control unit 710 controls the inner pressure of the fluid accommodation portion 765 to approach the target pressure value that is determined corresponding to the intensity of ejection set by the ejection intensity switching switch 627.

Here, for example, when the pump control unit 710 receives the intensity of ejection set by the ejection intensity switching switch 627 via the communication cable 640 from the drive control unit 600, the pump control unit 710 determines the target pressure value of the fluid accommodation portion 765 by referring to a table (not illustrated) in which the intensity of ejection and the target pressure value are correspondingly mapped and is stored in the memory 712.

For example, the pump control unit 710 determines the rough window upper limit value by adding a first predetermined value to the target pressure value, and the rough window lower limit value by subtracting the first predetermined value from the target pressure value. Similarly, the pump control unit 710 determines the fine window upper limit value by adding a second predetermined value less than the first predetermined value to the target pressure value, and the fine window lower limit value by subtracting the second predetermined value from the target pressure value.

As such, the fine window and the rough window are pressure ranges determined with respect to the target pressure value as a reference point, and the range of the fine window is narrower than that of the rough window.

For example, the rough window is determined as a pressure range in which the intensity of ejection specified by the practitioner can be changed to the extent that the practitioner does not feel uncomfortable about the changed intensity of ejection.

For this reason, in the embodiment, even though the inner pressure of the fluid accommodation portion 765 enters the rough window but the inner pressure does not agree with the target pressure value, the fluid ejection device 1 ejects the fluid from the pulsation generator 100 when the pulsation generator start-up switch 625 is operated. In this manner, for example, it is possible to start the ejection of the fluid without waiting for the completion of the adjustment of the inner pressure of the fluid accommodation portion 765, and to quickly and smoothly perform an operation.

In the embodiment, when the inner pressure of the fluid accommodation portion 765 is the rough window upper limit value or higher, even though the pulsation generator start-up switch 625 is operated, the fluid ejection device 1 does not eject the fluid from the pulsation generator 100. Accordingly, it is possible to prevent the fluid from being strongly ejected, which is unintended by the practitioner.

In the embodiment, also, when the inner pressure of the fluid accommodation portion 765 is the rough window lower limit value or lower, even though the pulsation generator start-up switch 625 is operated, the fluid ejection device 1 does not eject the fluid from the pulsation generator 100. In this manner, it is possible to prevent the weak intensity of ejection from causing the practitioner not to be able to precisely incise or exercise a target portion, that is, it is possible to prevent the fluid from uselessly ejected.

In a case where the inner pressure of the fluid accommodation portion 765 is controlled to approach the target pressure value, and reaches the target pressure value, even though the inner pressure of the fluid accommodation portion 765 is different from the target pressure value, the fluid ejection device 1 does not control the inner pressure to approach the target pressure value when the inner pressure is in the fine window. In this manner, it is possible to prevent the pump control unit 710 from continuously outputting a drive signal to the motor 730 so as to move the slider 720, regardless that the difference between the inner pressure of the fluid accommodation portion 765 and the target pressure value is very small enough not to affect the intensity of ejection any more.

In a case where the inner pressure of the fluid accommodation portion 765 is controlled to approach the target pressure value, and reaches the target pressure value, the fluid ejection device 1 controls the fluid pressing unit 732 in order for the inner pressure of the fluid accommodation portion 765 to enter the fine window when the inner pressure is in the rough window but not in the fine window.

When the inner pressure of the fluid accommodation portion 765 is in the rough window but is out of the fine window, the pump control unit 710 finely controls the fluid pressing unit 732 in such a manner that the pressure enters the fine window, which is referred to a fine adjustment operation in the following description.

When the pump control unit 710 performs the fine adjustment operation, the pump control unit 710 outputs a single drive signal (a single movement command) to the fluid pressing unit 731 in such a manner that the slider 720 moves by a predetermined very short distance. The drive signal output from the pump control unit 710 to perform the fine adjustment operation contains distance information that specifies a movement distance of the slider 720. The fluid pressing unit 731 drives the motor 730 in such a manner that the slider 720 moves by the specified movement distance.

When the pump control unit 710 performs the fine adjustment operation, the pump control unit 710 confirms whether the inner pressure of the fluid accommodation portion 765 is in the fine window after outputting the drive signal. When the inner pressure of the fluid accommodation portion 765 is in the fine window, the pump control unit 710 ends the control, and when the inner pressure is not in the fine window and is separated from the fine window, the pump control unit 710 outputs a drive signal to move the slider 720 again by the predetermined very short distance.

(A) in FIG. 7 indicates a time when the slider 720 comes into contact with the plunger 762, and an increase in the inner pressure of the fluid accommodation portion 765 starts, in a case where the pump control unit 710 moves the slider 720 in the push-in direction.

Since the inner pressure of the fluid accommodation portion 765 is out of the rough window at the time (A) in FIG. 7, the pump control unit 710 controls the fluid pressing unit 731 in such a manner that the inner pressure of the fluid accommodation portion 765 agrees with the target pressure value.

When the inner pressure of the fluid accommodation portion 765 is out of the rough window, the pump control unit 710 roughly controls the fluid pressing unit 732 in such a manner that the pressure agrees with the target pressure value, which is referred to a rough adjustment operation in the following description.

Unlike the fine adjustment operation, when the pump control unit 710 performs the rough adjustment operation, the pump control unit 710 outputs a drive signal in order for the slider 720 to continuously move until the inner pressure of the fluid accommodation portion 765 agrees with the target pressure value. The drive signal output from the pump control unit 710 to perform the rough adjustment operation does not distance information that specifies a predetermined very short movement distance of the slider 720.

As illustrated by (B) in FIG. 7, the inner pressure of the fluid accommodation portion 765 approaches the target pressure value by virtue of the rough adjustment operation performed by the pump control unit 710.

When the inner pressure of the fluid accommodation portion 765 reaches the fine window lower limit value ((C) in FIG. 7), and then reaches the target pressure value ((D) in FIG. 7), the pump control unit 710 instructs the fluid pressing unit 731 to stop the movement of the slider 720 in the push-in direction. Then, the slider 720 stops ((E) in FIG. 7).

Subsequently, the pump control unit 710 compares the inner pressure of the fluid accommodation portion 765 with the upper limit value and the lower limit value for the fine window, and the upper limit value and the lower limit value for the rough window.

Specifically, the pump control unit 710 compares the detected level data output from the AD converter 713 with the rough window upper limit value data, the rough window lower limit value data, the fine window upper limit value data, and the fine window lower limit value data.

As illustrated by (E) in FIG. 7, when the inner pressure of the fluid accommodation portion 765 exceeds the fine window lower limit value and is less than the fine window upper limit value, the pump control unit 710 does not control the inner pressure of the fluid accommodation portion 765 to approach the target pressure value, and the slider 720 remains stopped.

Since the gasket 763 mounted at the tip of the plunger 762 has elasticity, for awhile after the slider 720 is stopped, the inner pressure of the fluid accommodation portion 765 decreases until the contraction of the gasket 763 is stabilized.

For this reason, as illustrated by (F) in FIG. 7, a decrease in the inner pressure of the fluid accommodation portion 765 starts. When the inner pressure of the fluid accommodation portion 765 is the fine window lower limit value or less, the pump control unit 710 starts the fine adjustment operation in such a manner that the inner pressure of the fluid accommodation portion 765 enters the fine window. That is, the pump control unit 710 outputs a single drive signal (a single movement command) to the fluid pressing unit 731 in such a manner that the slider 720 moves by the predetermined very short distance ((G) in FIG. 7).

The inner pressure of the fluid accommodation portion 765 increases ((H) in FIG. 7), and decreases again due to the contraction of the gasket 763 ((I) in FIG. 7). When the inner pressure of the fluid accommodation portion 765 is the fine window lower limit value or less, the pump control unit 710 performs the fine adjustment operation again ((J) in FIG. 7).

While this process is repeatedly performed ((F) to (P) in FIG. 7), the contraction of the gasket 763 becomes stabilized, and in the example illustrated in FIG. 7, the drive signal (the movement command) is output five times so as to move the slider 720 for a fine adjustment from when the inner pressure of the fluid accommodation portion 765 enters the fine window ((C) in FIG. 7) to when the inner pressure is not out of the fine window ((Q) in FIGS. 7) ((G), (J), (L), (N), and (P) of FIG. 7).

As the contraction of the gasket 763 is stabilized, the interval between the fine adjustments increases gradually ((G), (J), (L), (N), (P) in FIG. 7), and finally, the inner pressure of the fluid accommodation portion 765 is stabilized and does not decrease below the fine window lower limit value or less any more ((Q) in FIG. 7).

That is, as the contraction of the gasket 763 is stabilized, the movement speed of the slider 720 decreases gradually, and when the inner pressure of the fluid accommodation portion 765 is stabilized and does not decrease below the fine window lower limit value or less any more, the slider 720 is stopped.

Here, it is possible to calculate the movement speed of the slider 720 by summing up the values of the distance information contained in one or more drive signals (movement commands) output from the pump control unit 710 during a unit time of t.

Specifically, the pump control unit 710 obtains the movement speed of the slider 720 by repeatedly calculating a total value of the distance information contained in the drive signals output during the past unit time of t while the time for calculating the movement speed of the slider 720 is shifted by a predetermined time as illustrated by t1, t2, . . . , tn in FIG. 7.

Since the pump control unit 710 starts the calculation of the movement speed of the slider 720 when the inner pressure of the fluid accommodation portion 765 enters the fine window (that is, when the difference between the inner pressure of the fluid accommodation portion 765 and the target pressure value is less than the second predetermined value ((C) in FIG. 7)), the movement speed of the slider 720 is initially calculated after a unit time of t has elapsed ((R) in FIG. 7).

Thereafter, at every the predetermined time, the pump control unit 710 calculates the movement speed of the slider 720 by summing up the distance information contained in the drive signals during the past unit time of t.

For example, in the fine adjustment operation, when a movement distance of the slider 720 specified by a single drive signal is a constant distance a, the movement speed of the slider 720 during the time period t1 illustrated in FIG. 7 is 4×a/t. Similarly, the movement speed of the slider 720 during the time period t2 is 3×a/t, and the movement speed of the slider 720 during a time period tn is 2×a/t.

Since a unit time of t used for the calculation of the movement speed of the slider 720 is constant, a total value of the movement distances of the slider 720 during a unit time of t may be used as the movement speed. In this case, specifically, the movement speed of the slider 720 during the time period t1 is 4×a. Similarly, the movement speed of the slider 720 during the time period t2 is 3×a, and the movement speed of the slider 720 during the time period tn is 2×a.

All of the movement speeds of the slider 720 decrease gradually as the contraction of the gasket 763 is stabilized.

For this reason, the pump control unit 710 can determine whether the channel is closed by the pinch valve 750, based on whether the movement speed of the slider 720 is a predetermined speed or higher when a predetermined amount of time (T) has elapsed ((S) in FIG. 7) after the difference between the inner pressure of the fluid accommodation portion 765 and the target pressure value becomes less than the second predetermined value ((C) in FIG. 7).

In the embodiment, when the movement speed of the slider 720 is the predetermined speed or higher after the predetermined amount of time (T) has elapsed, the pump control unit 710 determines that the channel is not closed by the pinch valve 750.

When the pump control unit 710 does not output all of the drive signals (the movement commands) during the predetermined time t, a total value of the distance information is calculated as zero.

Figure 8:
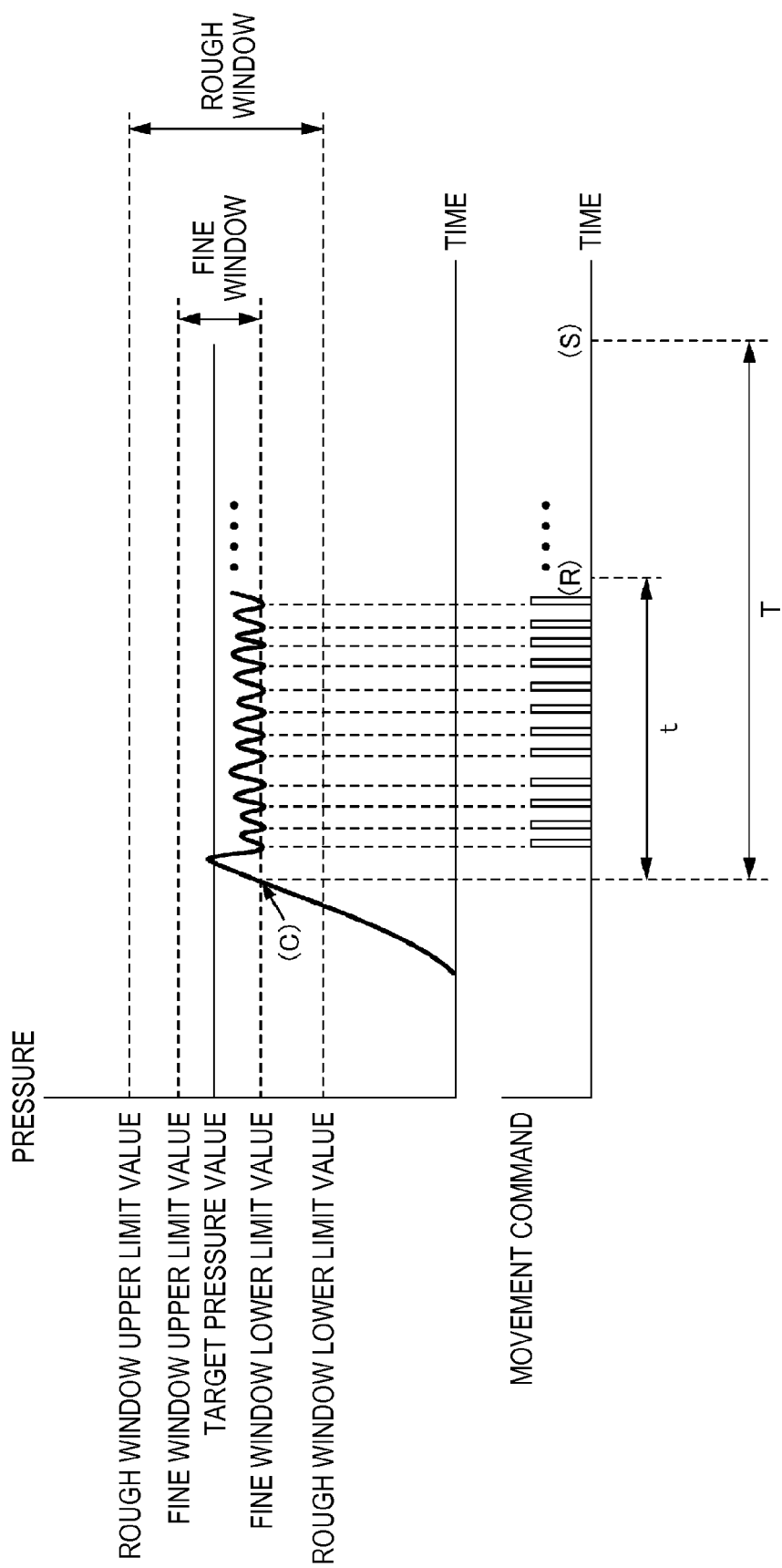
FIG. 8 is a graph illustrating a transition in the inner pressure of the fluid accommodation portion according to the embodiment of the invention.

Subsequently, FIG. 8 illustrates a case in which the pump control unit 710 controls the inner pressure of the fluid accommodation portion 765 to approach the target pressure value in a state where the connection tube 25 is not mounted on the pinch valve 750.

This case is the same as the case illustrated in FIG. 7 in that the inner pressure of the fluid accommodation portion 765 decreases due to the contraction of the gasket 763 after the inner pressure of the fluid accommodation portion 765 reaches the target pressure value and the movement of the slider 720 is stopped. In contrast, since the connection tube 25 is not clamped by the pinch valve 750, the fluid in the fluid accommodation portion 765 continuously flows out of the nozzle 211 of the pulsation generator 100.

For this reason, compared to when the connection tube 25 is mounted on the pinch valve 750, the inner pressure of the fluid accommodation portion 765 decreases below the fine window lower limit value much rapidly. Even though the pump control unit 710 performs the fine adjustment operation to move the slider 720 by the predetermined distance because the inner pressure of the fluid accommodation portion 765 is in the fine window, the amount of increase in the inner pressure of the fluid accommodation portion 765 is small, compared to when the connection tube 25 is mounted on the pinch valve 750.

Since the fluid in the fluid accommodation portion 765 continuously flows out of the nozzle 211 even after the contraction of the gasket 763 is stabilized, as illustrated in FIG. 8, the pump control unit 710 continuously performs the fine adjustment operation highly frequently.

For this reason, when the connection tube 25 is not mounted on the pinch valve 750, the movement speed of the slider 720 during a unit time of t is high, and a decrease in the movement speed over time is small, compared to when the connection tube 25 is mounted on the pinch valve 750.

Figure 9:
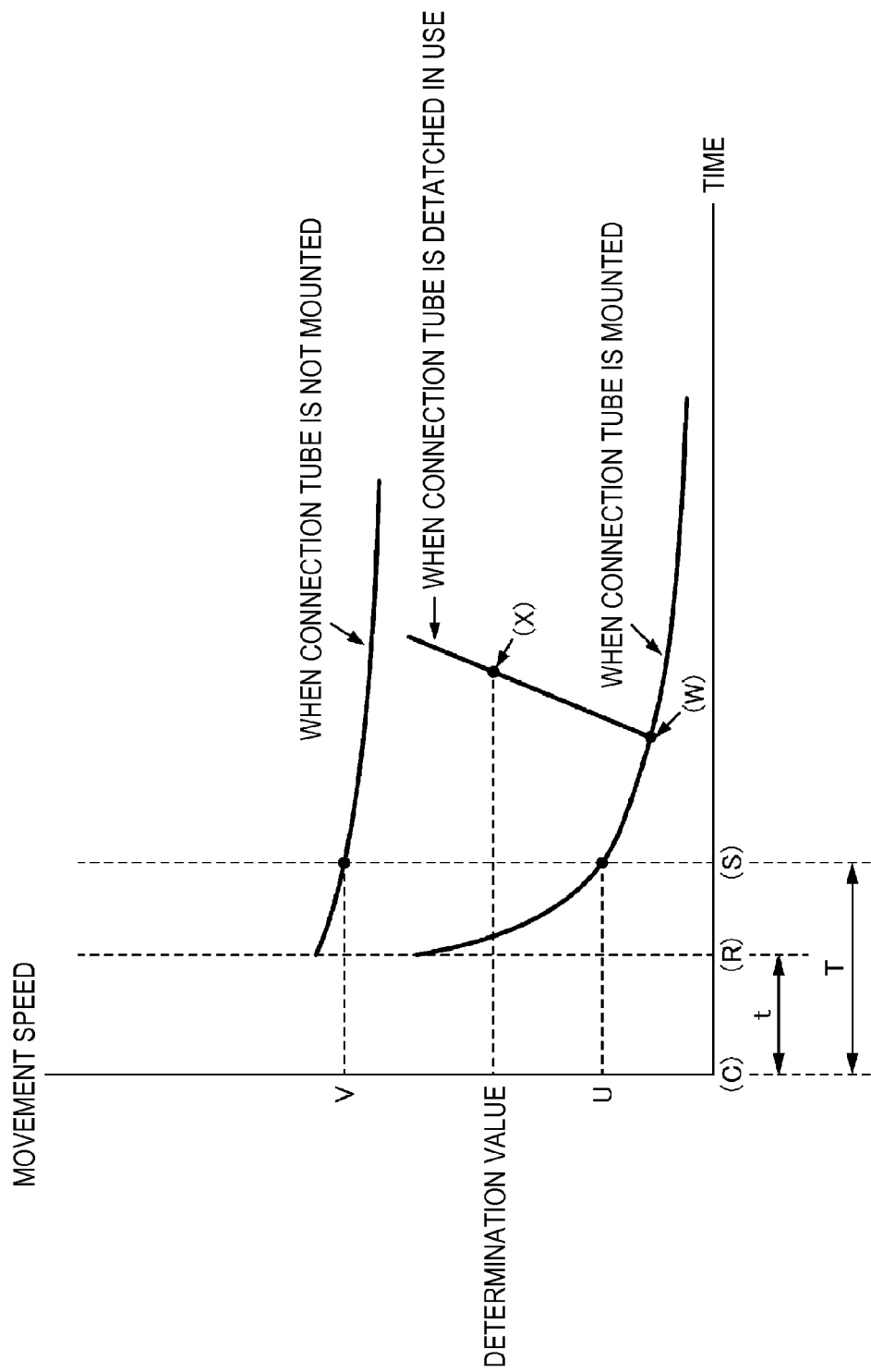
FIG. 9 is a graph illustrating a transition in the movement speed of a slider according to the embodiment of the invention.

FIG. 9 illustrates a change in the movement speed of the slider 720 over time when the connection tube 25 is mounted on the pinch valve 750, and when the connection tube 25 is not mounted on the pinch valve 750.

As illustrated in FIG. 9, the movement speeds of the slider 720 are sequentially calculated from a time (R) when a unit time of t has elapsed from the time (C) when the difference between the inner pressure of the fluid accommodation portion 765 and the target pressure value is less than the second predetermined value.

When the connection tube 25 is correctly mounted on the pinch valve 750, the movement speed of the slider 720 decreases gradually over time, a movement speed (U) is less than a determination value (a predetermined speed), and here, the movement speed (U) is a speed at a time (S) when the predetermined time T has elapsed from the time (C) when the difference between the inner pressure of the fluid accommodation portion 765 and the target pressure value is less than the second predetermined value.

In contrast, when the connection tube 25 is not mounted on the pinch valve 750, the movement speed of the slider 720 decreases gradually over time, and a movement speed (V) is not less than the determination value (the predetermined speed), and here, the movement speed (V) is a speed at a time (S) when the predetermined time T has elapsed from the time (C) when the difference between the inner pressure of the fluid accommodation portion 765 and the target pressure value is less than the second predetermined value.

In the embodiment, in a case where a movement speed of the slider 720 is the determination value (the predetermined speed) or higher when the predetermined time T has elapsed from the time (C) when the difference between the inner pressure of the fluid accommodation portion 765 and the target pressure value is less than the second predetermined value, the fluid ejection device 1 determines that the channel is not closed by the pinch valve 750.

In this manner, the fluid ejection device 1 can detect that the fluid channel cannot be closed by the pinch valve 750.

For example, the connection tube 25 may be detached from the pinch valve 750 in use, and the fluid ejection device 1 according to the embodiment can also detect this case.

In this case, when the connection tube 25 is detached from the pinch valve 750, the fluid in the fluid accommodation portion 765 starts leaking out of the nozzle 211. For this reason, an increase in the movement speed of the slider 720 starts from a time ((W) in FIG. 9) when the connection tube 25 is detached from the pinch valve 750.

When the movement speed of the slider 720 exceeds the determination value ((X) in FIG. 9), the pump control unit 710 determines that the channel is not closed by the pinch valve 750.

For this reason, the pump control unit 710 can detect whether the connection tube 25 is detached from the pinch valve 750 in use based on the combination of the following comparisons: comparison between the predetermined speed and the movement speed of the slider 720 at the time (S) when the predetermined time T has elapsed from the time (C) when the difference between the inner pressure of the fluid accommodation portion 765 and the target pressure value is less than the second predetermined value; and comparison between the predetermined speed and the movement speed of the slider 720 at an arbitrary time thereafter.

Specifically, in a case where at the time (S) when the predetermined time T has elapsed from the time (C) when the difference between the inner pressure of the fluid accommodation portion 765 and the target pressure value is less than the second predetermined value, the movement speed of the slider 720 is lower than the predetermined speed, and thereafter, the movement speed of the slider 720 at an arbitrary time is the predetermined speed or higher, the pump control unit 710 detects whether the connection tube 25 is detached from the pinch valve 750 in use.

Figure 10:
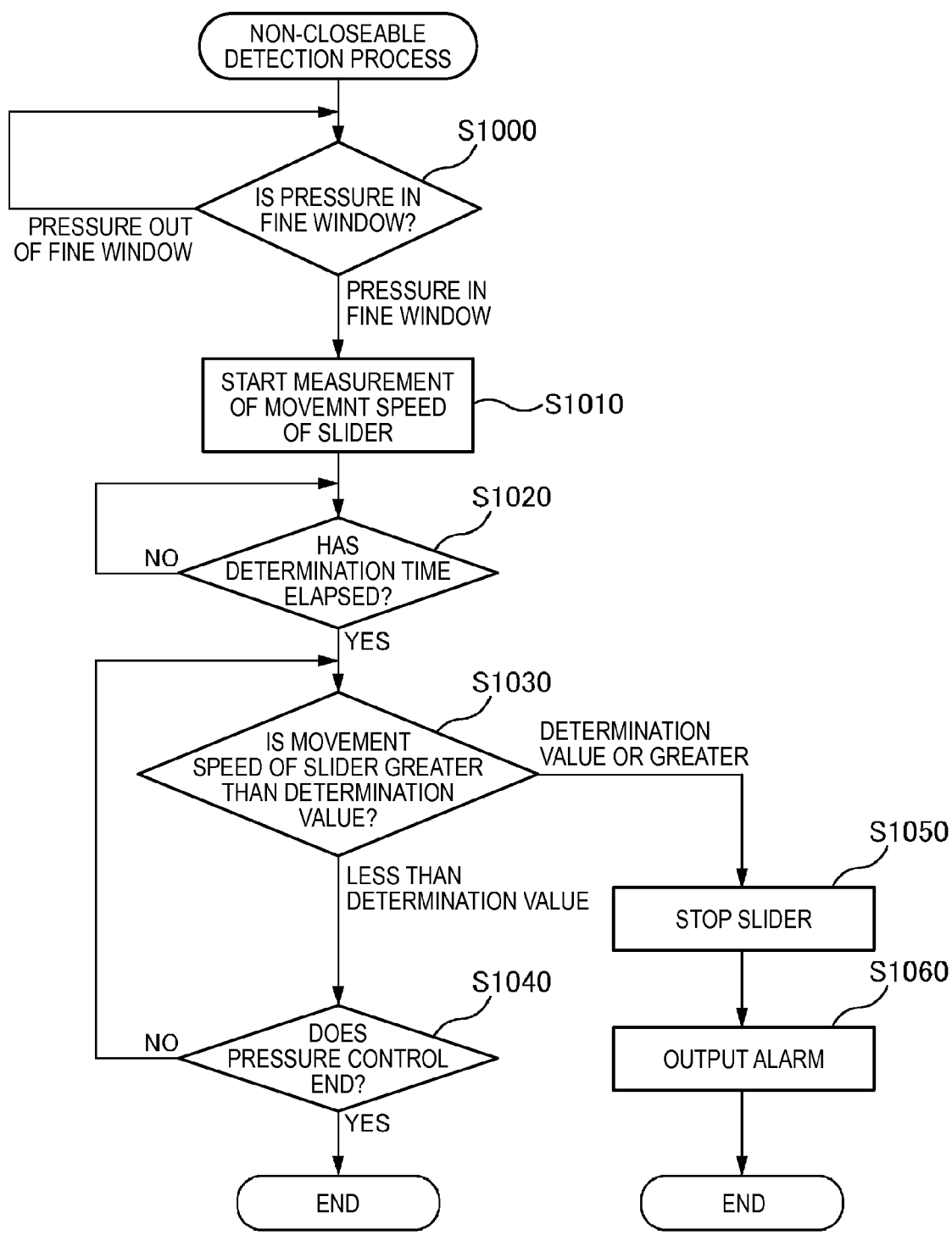
FIG. 10 is a flowchart illustrating a flow of a process of the fluid ejection device according to the embodiment of the invention.

FIG. 10 is a flowchart illustrating a flow of a process of detecting that the channel in the connection tube 25 cannot be closed by the pinch valve 750, the process being performed by the CPU 711.

First, the CPU 711 determines whether the inner pressure of the fluid accommodation portion 765 is in the fine window (S1000). When the inner pressure of the fluid accommodation portion 765 is less than the fine window upper limit value, and exceeds the fine window lower limit value, the CPU 710 determines that the inner pressure of the fluid accommodation portion 765 is in the fine window.

When the inner pressure of the fluid accommodation portion 765 is in the fine window, the CPU 711 starts the measurement of the movement speed of the slider 720 (S1010).

After the predetermined time T has elapsed (S1020), the CPU 711 compares the movement speed of the slider 720 with the determination value (S1030).

When the movement speed of the slider 720 is less than the determination value, the CPU 711 determines that the channel in the connection tube 25 is closed by the pinch valve 750.

The CPU 711 continuously monitors the movement speed of the slider 720 until the controlling of the inner pressure of the fluid accommodation portion 765 ends (S1030 and S1040). As described above, the controlling of the inner pressure of the fluid accommodation portion 765 ends when the practitioner operates the pulsation generator start-up switch 625, or when the fluid is ejected from the pulsation generator 100.

In contrast, when the movement speed of the slider 720 is the determination value or greater in S1030 (S1030), the CPU 711 determines that the channel in the connection tube 25 is closed by the pinch valve 750.

In this case, the CPU 711 outputs a drive signal for stopping the slider 720 to the press control unit 731, and stops the slider 720 (S1050).

In this manner, it is possible to stop the leakage of the fluid via the nozzle 211 of the pulsation generator 100.

The CPU 711 outputs a predetermined alarm indicative of a non-closed state of the channel (S1060). For example, the CPU 711 controls a speaker 790 to generate a predetermined alarm sound. In this manner, it is possible to promptly notify the practitioner that the connection tube 25 is not clamped by the pinch valve 750 by outputting the predetermined alarm.

The fluid ejection device 1 according to the embodiment has been described, and the fluid ejection device 1 according to the embodiment can detect that the fluid channel cannot be closed by the pinch valve 750. More specifically, the fluid ejection device 1 can detect a case in which the connection tube 25 is not correctly mounted on the pinch valve 750, a case in which the connection tube 25 is detached from the pinch valve 750, or a case in which the pinch valve 750 cannot close the connection tube 25 due to a failure.

Accordingly, it is possible to improve the user-friendliness and the safety of the fluid ejection device 1.

In the example of the embodiment, the fluid ejection device 1 calculates the movement speed of the slider 720 by summing up the values of the distance information contained in the drive signals output from the pump control unit 710 to the fluid pressing unit 731 during a unit time of t when the pump control unit 710 performs the fine adjustment operation; however, the fluid ejection device 1 may calculate the movement speed of the slider 720 by obtaining movement distances of the slider 720 using an encoder for detecting a rotation frequency of the motor 730, and summing up the movement distances during a unit time of t.

In the example of the embodiment, at the time ((S) in FIG. 7) when the predetermined time T has elapsed from the time ((C) in FIG. 7) when the difference between the inner pressure of the fluid accommodation portion 765 and the target pressure value is less than the predetermined value (the second predetermined value that specifies the width of the fine window), the movement speed of the slider 720 is compared with the predetermined speed; however, the predetermined value can be determined as an arbitrary value, and for example, the predetermined value is set to zero, and when the predetermined time T has elapsed from the time ((D) in FIG. 7) when the inner pressure of the fluid accommodation portion 765 exceeds the target pressure value, the movement speed of the slider 720 may be compared with the predetermined speed.

The embodiment is presented so as to help the understanding of the invention, and does not limit the interpretation of the invention. Modifications and improvements can be made to the invention insofar as the modifications and the improvements do not depart from the spirit of the invention, and the equivalents are also included in the invention.

What is claimed is:

1. A fluid ejection device comprising:
    a fluid container that has a fluid accommodation portion for accommodating a fluid, and a fluid outlet formed in the fluid accommodation portion;
    a fluid pressing unit that moves in a pressing direction according to a movement command, and presses the fluid accommodation portion to cause the fluid to flow out of the fluid outlet;
    a connection tube, one end of which is connected to the fluid outlet;
    a fluid ejection unit that has a fluid intake port connected to the other end of the connection tube, and ejects in a pulsed manner the fluid taken in via the fluid intake port;
    a pressure detection unit that detects an inner pressure of the fluid accommodation portion;
    a channel opening and closing unit that opens and closes a channel of the fluid in the connection tube;
    a press control unit that outputs the movement command to the fluid pressing unit and controls the inner pressure of the fluid accommodation portion to approach a predetermined target pressure value, in a state where the channel is closed by the channel opening and closing unit;
    a movement speed acquisition unit that acquires a movement speed of the fluid pressing unit; and
    a channel determination unit configured to determine that the channel is not closed by the channel opening and closing unit, in a case where the movement speed of the fluid pressing unit is a predetermined speed or higher when a predetermined amount of time has elapsed after a difference between the inner pressure of the fluid accommodation portion and the target pressure value becomes less than a predetermined value.

2. The fluid ejection device according to claim 1, wherein the movement command output from the press control unit contains distance information that specifies a movement distance of the fluid pressing unit, and wherein the movement speed acquisition unit calculates the movement speed of the fluid pressing unit by summing up the values of the distance information contained in one or more movement commands that the press control unit outputs during a unit time.

3. The fluid ejection device according to claim 1, wherein when it is determined that the channel is not closed by the channel opening and closing unit, the press control unit stops the fluid pressing unit.

4. The fluid ejection device according to claim 1, wherein when it is determined that the channel is not closed by the channel opening and closing unit, the channel determination unit outputs a predetermined alarm.

* * * * *